United States Patent
Kono et al.

[19]

[11] Patent Number: 5,811,203
[45] Date of Patent: Sep. 22, 1998

[54] DISPLAY DEVICE OF STORAGE BATTERY

[75] Inventors: Toshihiko Kono; Syuuichi Yamaguchi, both of Kurume, Japan

[73] Assignee: Daiden Co., Ltd., Japan

[21] Appl. No.: 743,678

[22] Filed: Nov. 6, 1996

[30] Foreign Application Priority Data

| Jan. 12, 1996 | [JP] | Japan | 8-000427 |
| Feb. 29, 1996 | [JP] | Japan | 8-071104 |
| Jun. 21, 1996 | [JP] | Japan | 8-006627 |

[51] Int. Cl.$^6$ .................................. H01M 10/48
[52] U.S. Cl. ................. 429/91; 73/451; 73/32 R
[58] Field of Search .............. 429/91; 73/32 R, 73/451; 356/136

[56] References Cited

U.S. PATENT DOCUMENTS

| 3,895,964 | 7/1975 | Sakamoto | 429/91 |
| 4,320,291 | 3/1982 | Uramoto | 429/91 X |
| 4,989,453 | 2/1991 | Hiiesalu | 429/91 X |
| 5,180,643 | 1/1993 | Nedbal | 429/91 |

FOREIGN PATENT DOCUMENTS

| 49-47822 | 8/1972 | Japan . |
| 53-51768 | 5/1978 | Japan . |
| 54-54244 | 4/1979 | Japan . |
| 58-7468 | 1/1983 | Japan . |
| 6-243900 | 9/1994 | Japan . |

*Primary Examiner*—Stephen Kalafut
*Attorney, Agent, or Firm*—Rader, Fishman, & Grauer; Ronald P. Kananen

[57] ABSTRACT

A display device of a storage battery for optically displaying a condition of an electrolytic solution stored in a casing of the storage battery comprises a pillar member having a transparent body having one end and other opposite end, the one end of the pillar member being engaged at an upper surface of the casing in a usable state so that the other opposite end thereof projects into the casing. An inclined end surface of the opposite end side thereof is inclined to a side surface of the pillar member at a predetermined angle so that an incident light transmitting from the one end side thereof permeates through the inclined end surface or is reflected thereby according to the condition of the electrolytic solution which is in contact with the inclined end surface. The display device further comprises a display member provided with display surfaces on which the light permeating through the inclined end surface or reflected thereby is projected, the display surfaces being different from each other to optically display the condition of the electrolytic solution.

15 Claims, 18 Drawing Sheets

SOLUTION INSUFFICIENCY

CAPACITY INSUFFICIENCY

SUFFICIENCY

DISPLAY DEVICE OF STORAGE BATTERY

BACKGROUND OF THE INVENTION

The present invention relates to a display device of a storage battery for displaying the condition thereof and is particularly intended for simplifying the structure of the display device.

As a device for optically detecting or displaying specific gravity of an electrolytic solution of a storage battery by utilizing relationship between the specific gravity and a refractive index, there are publicly known such devices as disclosed in many publications.

The specific gravity detecting device, which is disclosed, for example, in the Japanese Non-examined Patent Publication NO. SHO 53-51768 or the Japanese Non-examined Patent Publication NO. SHO 54-54244, has a light source which projects a light to a pointed end surface of a rod-shaped light permeation body immersed in the electrolytic solution and is adapted to detect the specific gravity of the electrolytic solution on the basis of the proportion of the amount of the light which permeates through the pointed end surface thereof to the amount of the light which is reflected by the pointed end surface thereof.

The display device, which is disclosed in the Japanese Non-examined Patent Publication NO. SHO 53-51768, has a cone-shaped transparent rod, the pointed end of which is immersed in the electrolytic solution and a spherical float member having the predetermined specific gravity. The display device is operated in such a manner that, according to the change of the specific gravity of the electrolytic solution, the spherical float member floats in the electrolytic solution so that the spherical float member comes into contact with the pointed end of the cone-shaped transparent rod and the spherical float member sinks therein so that the spherical float member goes away from the pointed end thereof. That is, the display device is adapted to optically indicate the change of the specific gravity of the electrolytic solution on the basis of the floating and sinking motions of the spherical float member.

The display device, which is disclosed in the Japanese Non-examined Utility Model Publication NO. SHO 58-7468, has a rod-shaped transparent rod one end surface of which projects into the upper surface of the storage battery and other pointed end of which is immersed in the electrolytic solution. The display device has a fixed display member secured through a shaft at the lower end of the pair of the leg portions extending from the rod-shaped body so that the fixed display member is disposed in the electrolytic solution, the display device being located within the area that the operator can view from the one end surface of the rod-shaped body. The display device also has a rotational display member (rotational specific gravity float member), which is within the electrolytic solution that the operator enables to view from the one end surface of the rod pivotally mounted on the shaft so that the rotational display member is rotated around the shaft and the fixed display member. The pivotally mounted portion of the rotational display member on the shaft is located at the position apart from the center of gravity thereof in order to locate the center of the rotational display member on which buoyancy acts at the position which is different from any positions on the shaft. The specific gravity of the rotational display member is selected for rising and falling, i.e. sinking or lowering, the rotational display member according to the change of the specific gravity so as to rotate the rotational display member. In addition, the display phase of the surface of the rotational display member which faces upwardly and the display phase of the surface of the fixed display member which faces upward are changed each other. As a result, the display phase which the operator can view from the rod-shaped body is changed according to the rising and falling of the rotational display member on the basis of the change of the specific gravity through the electric discharge of the electrolytic solution so that it is possible to know the charged condition of the storage battery.

Moreover, the display device, which is disclosed in the Japanese Non-examined Utility Model Publication NO. SHO 49-47822, is shown in FIG. 18. A conventional display device 200 shown in FIG. 18 has a tubular body 201 formed of a transparent material and has a corrosion resistance, the lower end of which is located at the lower limit position in the electrolytic solution 57. A conical bottom body 202 having the 45° inclined surface is joined in communication with the lower end of the tubular body 201. The silver mirror surface 204 is formed at the inclined surface portion of the bottom of the tubular body 201. The solution guide hole 205 is mounted at the center of the lower end of the tubular body 201, the hole 205 being communicated with the inside 203 of the tubular body 201. The spherical float member 206 is disposed in the inside 203 of the tubular body 201, the spherical float member 206 being formed of a color transparent material and having a specific gravity of nearly 1.2, the diameter of which is larger than that of the solution guide hole 205.

In the display device 200, owing to the spherical float member 206 having the specific gravity of nearly 1.2, when the specific gravity of the electrolytic solution 57 is not more than 1.2 or the electrolytic solution 57 is insufficient, the spherical float member 206 on the electrolytic solution 57 falls down to the lower end of the inside 203 of the tubular body 201 so that the float member 206 is located at the center concave portion of the silver mirror surface 204. As a result, when the operator views the tubular body 201 from the display surface on the cap thereof, the whole area of the bottom of the tubular body 201 is viewed in color because the silver mirror surface 204 reflects the color of the spherical float member 206. Moreover, when the level of the electrolytic solution 57 is suitable and the specific gravity of the electrolytic solution 57 is proper, the float member 206 floats on the surface of the electrolytic solution 57 so that the displayed color of the display surface is different from that of the display surface for situations where the specific gravity of the electrolytic solution 57 is not more than 1.2 or the electrolytic solution 57 is insufficient. Therefore, it is possible to observe the condition of the storage battery by viewing the tubular body from the display surface on the cap thereof. However, in the conventional display devices disclosed in the Publication NO. SHO 53-51768 and the Publication NO. SHO 54-54244, for machining the pointed end surface or other similar portion, the extreme accuracy is required and, because of using the source of light, the electrical signal processing is needed. In addition, the number of processes for construction of the display device are increased. For these reasons, the cost of manufacturing the display device rises.

Furthermore, because the display devices, which are disclosed in the Publication NO. SHO 53-51768 and in the Publication NO. SHO 58-7468, are constructed in such a manner that the operator looks directly at the diffused reflection light of the spherical float member or the rotational display member, the displayed image is restricted to the size of the float member or the display member. Therefore, it is difficult to display a large image. Especially, in the display device disclosed in the Publication NO. SHO 58-7468, because of using the rotational display member, the rotating motion of the rotational display member may not be performed smoothly so that detection errors regarding the specific gravity of the electrolytic solution may happen. Moreover, since a lot of parts of display device and movable portions are required, the number of processes for construction thereof are increased so that the cost of manufacturing the display device rises.

On the other hand, in the display device 200 shown in FIG. 18, the light transmitting from the outer periphery of the tubular body 201 is reflected by the silver mirror surface 204 and then the reflected right is irradiated to the spherical float member 206. The light permeating through the float member 206 is reflected by the silver mirror surface 204 again so as to return the reflected light to the upper end side of the tubular body 201. Therefore, the displayed image obtained by the display device 200 is of large size and bright. However, since the specific gravity of the electrolytic solution is detected on the basis of the movement of the float member 206, it is difficult to gain the extreme accuracy of the float member 206 to move the float member 206 smoothly and, for requiring the extreme accuracy, the manufacturing cost of the display device 200 rises. In addition, the rising and falling movement of the float member 206 may not be performed smoothly so that the specific gravity of the electrolytic solution will not be detected exactly.

Still furthermore, since the display device 200 needs the silver mirror surface 204, the number of processes for manufacturing and checking the display device 200 are increased and the manufacturing and checking cost of the display device 200 rises. Moreover, because of utilizing a sealed air layer in order to reflect the light by means of the silver mirror surface 204, the manufacturing cost thereof also rises.

SUMMARY OF THE INVENTION

An object of the present invention is to substantially eliminate defects or drawbacks encountered in the prior arts described above and to provide a display device of a storage battery which is capable of gaining a large and bright displayed image, the structure of the display device being simple, so that the manufacturing and checking cost and work of the display device is reduced.

Another object of the present invention is to provide an display device which is capable of improving the precision of detecting and displaying a specific gravity of an electrolytic solution, the structure of the display device being simple, so as to reduce the manufacturing and checking cost of the display device.

These and other objects of the present invention can be achieved by providing in one aspect a display device of a storage battery for optically displaying a condition of an electrolytic solution stored in a casing of the storage battery, the device comprising:

a cylindrical pillar member having a transparent body having one end and other opposite end, the one end of the pillar member being engaged at an upper surface of the casing in a usable state so that the other opposite end is projected into the casing, the transparent body of the cylindrical pillar member having an inclined end surface of the opposite end side having an inclination to a side surface of the pillar member at a predetermined angle so that an incident light transmitting from the one end side thereof permeates through the inclined end surface or is reflected according to a condition of the electrolytic solution which is in contact with the inclined end surface; and a display member provided with a plurality of display surfaces on which the light permeating through the inclined end surface or reflected thereby is projected, the display surfaces being different from each other to optically display the condition of the electrolytic solution.

In preferred embodiments, the display member is provided at the one end side of the pillar member, and each of the display surfaces is colored.

A physical condition of the electrolytic solution includes, for example, the specific gravity of the electrolytic solution and a surface level thereof.

The predetermined angle of the inclined end surface is set so that an incident angle of the incident light transmitting from the one end side on the inclined end surface is a predetermined critical angle, and the critical angle is set in accordance with optical quality of a material (such as index of refraction) of the pillar member and a characteristic feature of the electrolytic solution.

The inclined end surface is provided with a plurality of inclined surface portions, the inclined surface portions being inclined to the side surface of the pillar member at different predetermined angles, respectively, and the inclined end surface has a plurality of stages, which are continuously inclined to the side surface of the pillar member at different predetermined angles, respectively.

According to this structure of the present invention in this aspect, the incident light transmitting from the one end side of the cylindrical pillar member is reflected to the inclined surface of the opposite end side or permeates therethrough in accordance with the specific gravity of the electrolytic solution and a surface level thereof. Each of the reflected light and permeating light is projected onto each of the display surfaces, respectively, and the display phase of the display surf ace through which the light permeates and the display phase of the display surface by which the light is reflected are different from each other. As a result, the condition of the electrolytic solution is detected by the different display phases when the operator looks into the end surface of the one side of the pillar member.

Therefore, the display device can be constructed with simple structure in which the inclined surface is formed as a pillar member and the display member is provided at the one end side of the pillar member, making it possible to manufacture the display device easily, to improve quality of the display device and the yield thereof and to reduce the manufacturing cost of the display device. Moreover, because a movable portion of the display device is not moved according to the surface level of the electrolytic solution and specific gravity thereof, the detecting errors of the display device and the incorrect display operation thereof can be prevented.

In addition, the inclined surface portions are inclined to the side surface of the pillar member at different predetermined angles, respectively. Therefore, it is possible to change the condition of the reflection of the incident light from the condition of the permeation thereof according to each phases of the level of the specific gravity of the electrolytic solution and the surface level thereof. As a result, since the display phase gained in accordance with the conditions of the electrolytic solution are changed closely through the combination of the inclined surface portions, it is possible to distinguish each of the charge conditions thereof clearly.

Furthermore, when the inclined surface is formed with a plurality of stages, it is possible to divide the advancing direction of the light transmitting from the one end side so as to part the display phases according to each conditions of the electrolytic solution, thereby making it possible to display each conditions of the electrolytic solution in detail.

In another aspect of the present invention, there is provided a display device of a storage battery for optically displaying a condition of an electrolytic solution stored in a casing of the storage battery, the device comprising:

a cylindrical pillar member having a transparent body having one end and other opposite end, the one end of the pillar member being engaged at an upper surface of the casing in a usable state so that the other opposite end thereof is projected into the casing, the other opposite end being formed with a communication hole portion communicated with the electrolytic solution in the casing, through which the electrolytic solution is introduced into the cylindrical pillar member; and a specific gravity ball unit disposed in the communication hole portion the specific gravity ball unit having a predetermined specific gravity and rising and falling along a center axis of the communication hole portion in accordance with at least one of a surface level of the electrolytic solution in the communication hole portion and the specific gravity thereof, the transparent body of the cylindrical pillar member having an inclined surface of an opposite end side of the pillar member having an inclination to a side surface of the pillar member at a predetermined angle so as to reflect an incident light transmitting from the one end side thereof totally toward a communication hole portion side so as to optically display the condition of the electrolytic solution.

In preferred embodiments of this aspect, the displayed condition of the electrolytic solution is changed according to the rising and lowering movement of the specific gravity ball unit.

The communication hole portion is formed at about a center portion of the opposite end side of the pillar member.

The specific gravity ball unit is formed of a transparent material, and the specific gravity ball unit includes a plurality of spherical balls having specific gravities different from each other and being colored in different colors so that the displayed condition of the electrolytic solution is changed in accordance with the rising and lowering movement of each of the spherical balls.

The predetermined angle of the inclined surface is set so that an incident angle of the incident light transmitting from the one end side of the inclined end surface is a predetermined critical angle, and the critical angle is set in accordance with a quality of a material of the pillar member and a characteristic feature of the electrolytic solution.

The inclined surface has a plurality of stages which are continuously inclined to the side surface of the pillar member at different predetermined angles, respectively.

The display device of a storage battery further comprises a projecting portion formed so as to project into an upper end portion of the communication hole portion, the projecting portion having a pointed end portion formed to provide a cone shape so as to incline a surface of the pointed end portion at a predetermined angle so that the incident light transmitting from the one end side thereof permeates through the inclined surface of the pointed end portion or is reflected thereby according to the condition of the electrolytic solution which is in contact with the inclined surface thereof.

According to the structure of this aspect, the inclined angle of the inclined surface can be set so that the incident angle of the incident light transmitting from the one end side on the inclined surface is larger than the critical angle when the electrolytic solution having the maximum specific gravity, that is, the maximum refracting angle is in contact with the inclined surface, thereby reflecting the incident right totally at all times. The specific gravity ball rises and falls according to the surface level of the electric solution in the communication hole portion and the specific gravity, that is, charging condition, thereof. The incident light transmitting from the one end side and reflected totally by the inclined surface is projected onto a predetermined position (reflection layer or projection layer). If the specific gravity ball is located at the predetermined position, the reflected light is hit on the specific gravity ball and the light is reflected by the specific gravity ball or permeates therethrough. The reflected or permeating light is reflected totally by the inclined surface again, so that the reflected light is returned toward the one end side of the pillar member, thereby optically displaying the condition of the electrolytic solution.

Furthermore, the inclined surface which is the outer side surface of the pillar member is formed as the total reflection surface, making it possible to manufacture the display device easily. Moreover, since the large quantity of light can be projected onto the specific gravity ball and the large quantity of light reflected thereby or permeating therethrough is reflected totally by the inclined surface of the outside of the communication hole portion so as to return the total reflected light toward the end side of the pillar member, large and bright image can be gained. In addition, since the specific gravity ball which rises and falls in the communication hole portion according to the surface level of the electrolytic solution and specific gravity thereof are formed like a spherical shape, the rising and falling movement of the specific gravity ball can be made smooth.

Furthermore, as occasion demands, a plurality of specific gravity balls each having a spherical shape are disposed. The balls have specific gravities different from each other and are colored in different colors. Accordingly, the displayed condition of the electrolytic solution is changed in accordance with rising and falling positions of each of the spherical balls. Therefore, it is possible to display the various conditions of the specific gravity and surface level of the electrolytic solution clearly in plural colors so as to distinguish each conditions by different colors.

Moreover, when the inclined surface is formed with a plurality of stages, the total reflection of the incident light on the inclined surface is performed in plural times so that the advancing direction of the incident light can be turned on the large angle. Therefore, this structure is suitable for displaying the specific gravity of the electrolytic solution by the permeating light which is incident toward the transparent specific gravity ball from the side thereof.

In addition, the display device further comprises a projecting portion formed to project onto an upper end portion of the communication hole portion, and the projecting portion has a pointed end portion shaped like a cone so as to incline a surface of the pointed end portion at a predetermined angle so that the incident light transmitting from the one end side thereof permeates through the inclined surface of the pointed end portion and is reflected thereby according to the condition of the electrolytic solution which is in contact with the inclined surface thereof. Since it is possible to detect whether or not the gravity ball and the surface level of the electrolytic solution are in contact with the center inclined surface, it is possible to display the various conditions of the electrolytic solution in detail.

BRIEF DESCRIPTION OF THE DRAWINGS

The invention will be readily understood through the following description by way of the accompanying drawings illustrating preferred embodiments of the present invention.

In the accompanying drawings.

Figure 1A:
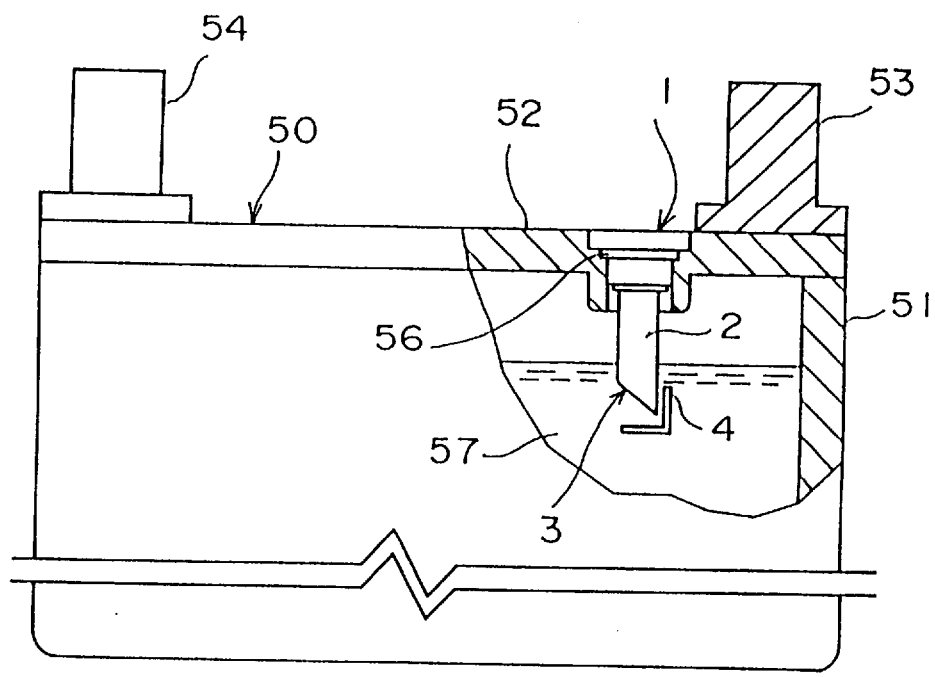
FIG. 1A is a front view of a storage battery fitted with a display device partially broken away, the display device being related to a first embodiment of the present invention
Figure 1B:
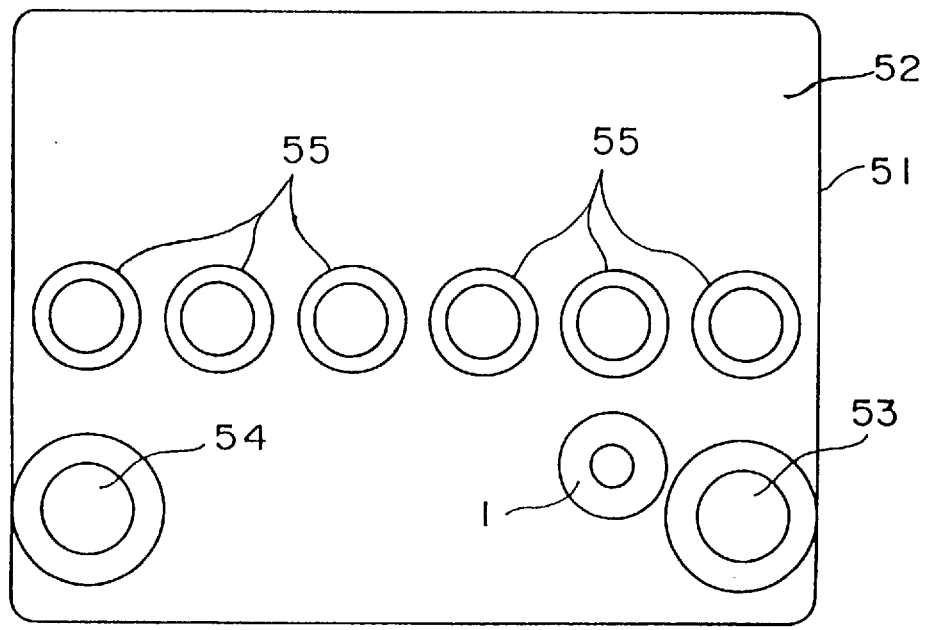
FIG. 1B is a plan view of the storage battery fitted with the display device related to the first embodiment of the present invention.
Figure 2A:
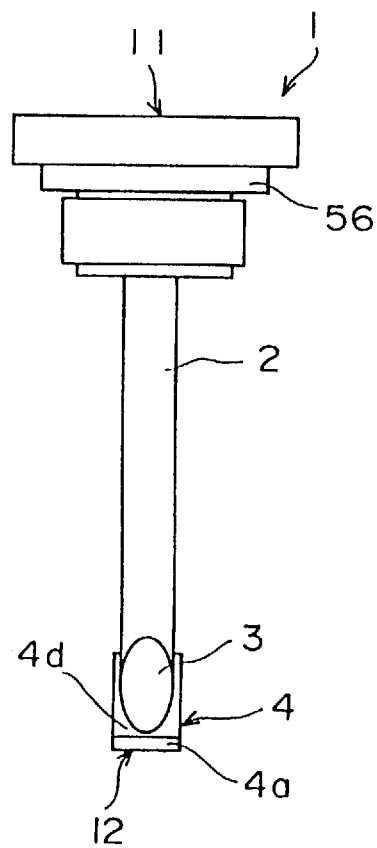
FIG. 2A is a side view of the storage battery related to the first embodiment of the present invention and FIG. 2B is a longitudinal sectional view related to the first embodiment of the present invention.
Figure 2B:
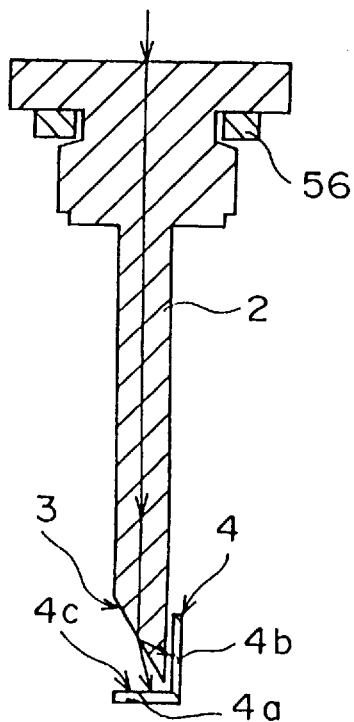
Figure 3:
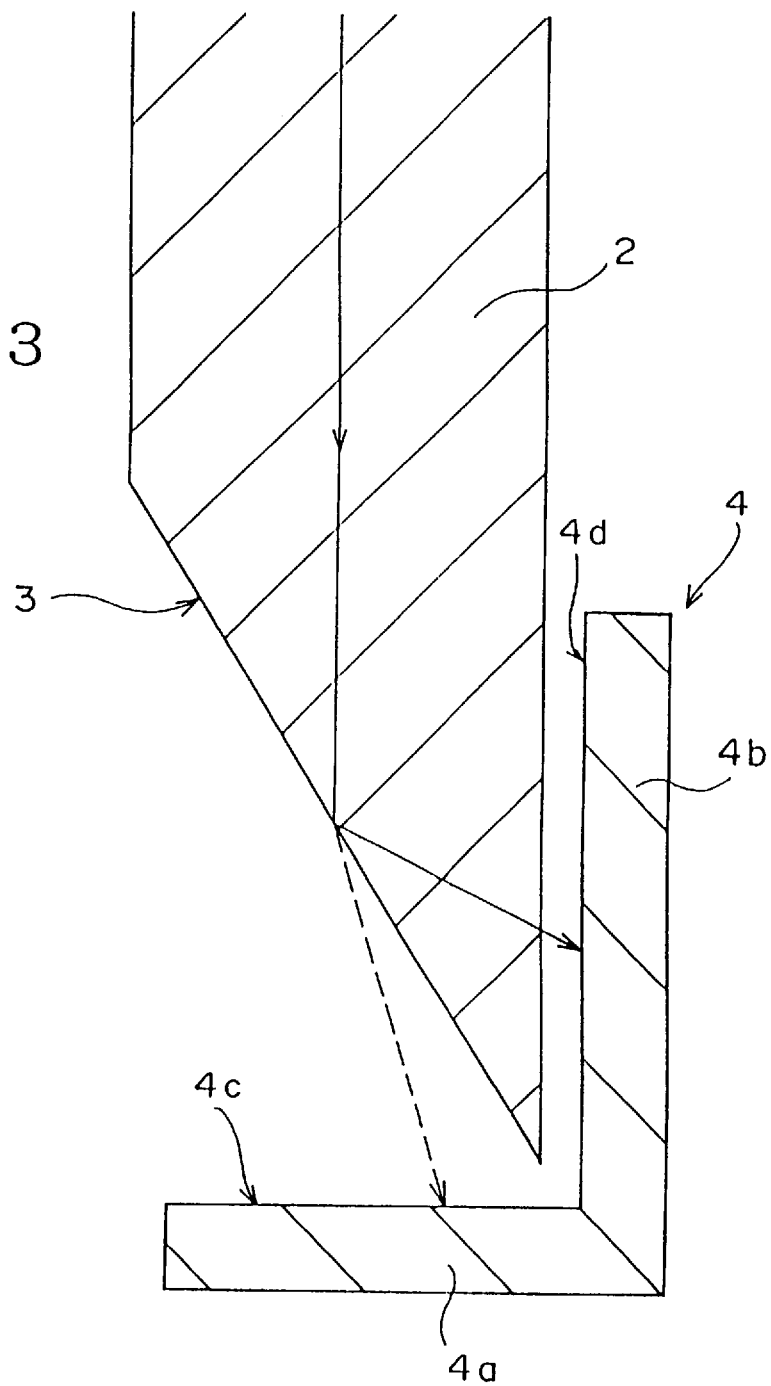
FIG. 3 is a longitudinal sectional view, in an enlarged scale, of a portion of the display device shown in FIG. 2B.

DESCRIPTION OF THE PREFERRED EMBODIMENTS (First embodiment)

A first preferred embodiment of the present invention will be described hereunder with reference to the illustration of FIGS. 1 to 4. This first embodiment shows a display device of the present invention which is applied to a lead storage battery.

Referring to FIGS. 1 to 4, a display device 1 related to the present embodiment has a transparent pillar member 2, one end 11 of which is fitted with the upper cover 52 of the storage battery 50, the pillar member 2 being shaped like a column and has a display member 4 having a blue surface 4c and red surface 4d. The end surface of the opposite end 12 side of the pillar member 2 is inclined to the side surface thereof so that an inclined surface 3 is formed. The light from the one end 11 side of the pillar member 2 which permeates through the inclined surface 3 or reflected thereby, is projected onto the blue surface 4c and the red surface 4d.

The pillar member 2 is formed from transparent polycarbonate, AS resin, acrylic resin, or other similar material, the one end 11 side (the upper end side) being expanded like a flange. A rubber packing 56 is fitted into the one end 11 side, which is fitted with the upper cover 52 having electrodes (or, more commonly, terminals) 53, 54 and liquid stoppers such as liquid plug 55. An electrolytic solution 57 is stored in a casing 51 of the storage battery 50.

The electrolytic solution 57 is prevented from leaking out of the casing 51 with the rubber packing 56 even if the electrolytic solution 57 is vibrated. The opposite end 12 side (lower end side) of the pillar member 2 is usually immersed in the electrolytic solution 57, the lower end thereof coinciding with the lowest limit level of the electrolytic solution 57.

The inclination angle of the inclined surface 3 formed at the opposite end 12 of the pillar member 2 is set so as to reflect the light transmitting from the one end 11 side totally by the inclined surface 3 when the electrolytic solution 57 is in contact with the inclined surface 3. The charging supply of the electrolytic solution 57 is insufficient and the specific gravity of the electrolytic solution 57 is smaller than that of the electrolytic solution 57 in a sufficient charging supply condition. For example, the concrete inclination angle of the inclined surface is set as follows. In the case where the pillar member 2 is made of polycarbonate, the refractive index of polycarbonate n1 is 1.585. Because the specific gravity of the electrolytic solution 57 in the sufficient charging supply condition is within the limit of 1.19 to 1.21, in the first embodiment, the lower limit value of 1.19 of the specific gravity thereof is used. That is, in the case of the specific gravity of the electrolytic solution 57 is 1.19, since the refractive index n2 thereof is 1.368, the critical angle is $\phi=59.67°$ according to $n2/n1=\sin\phi$. Therefore, since the inclination angle of the inclined surface 3 is set so that the incident angle of the light transmitting from the one end 11 side on the inclined surface is the critical angle of nearly 60°, in the case where the electrolytic solution 57 is not in contact with the inclined surface 3 because of the insufficiency of the electrolytic solution 57 and the charging supply of the electrolytic solution 57 is insufficient for the reason that the specific gravity of the electrolytic solution 57 which is in contact with the inclined surface 3 is smaller than the lower limit value thereof, the inclined surface 3 reflects reflect the light totally. In addition, in the case where the charging supply of the electrolytic solution 57 is sufficient for the reason that the specific gravity of the electrolytic solution 57 which is in contact with the inclined surface 3 is larger than the lower limit value thereof, the light permeates through the inclined surface 3. In the case of the insufficiency of the electrolytic solution and charging supply, the incident light on the inclined surface 3 is totally reflected sideward, the incident light permeates through the pillar member 2 toward the side thereof. On the other hand, in the case of the sufficiency of the charging supply, the incident light on the inclined surface 3 permeates through the pillar member 2 toward the lower side of the inclined surface 3 by the refracting angle according to the specific gravity of the electrolytic solution 57.

Moreover, a case in which the incident angle of the light transmitting from the one end 11 side on the inclined surface is about 60° is only one example. It is possible to set the incident angle at any optional angle in accordance with the quality of the material of the pillar member 2 and the characteristic feature of the electrolytic solution 57.

The display member 4 is provided at the opposite end 12 side of the pillar member 2. The display member 4 has a base plate portion 4a provided below and away from the inclined surface 3 and a stand-up (rising) portion 4b vertically mounted on the base plate portion 4a and provided toward the side of and away from the side surface of the pillar member 2 opposite to the inclined surface 3 thereof.

The light from the one end 11 side of the pillar member 2 which permeates through the inclined surface 3 is projected onto the upper surface of the base plate portion 4a. The light from the one end 11 side of the pillar member 2 which permeates through the inclined surface 3 is projected onto the side surface of the stand-up portion 4b. The upper surface of the base plate portion 4a of the display member 4 is the blue surface 4c colored in blue and the side surface of the stand-up portion 4b is the red surface 4d colored in red, the display phase of the upper surface of the base plate portion 4a and the side surface of the stand-up portion 4b being different from each other.

Next, the display condition of the structure of the display device 1 in this first embodiment will be described hereunder.

Figure 4A:
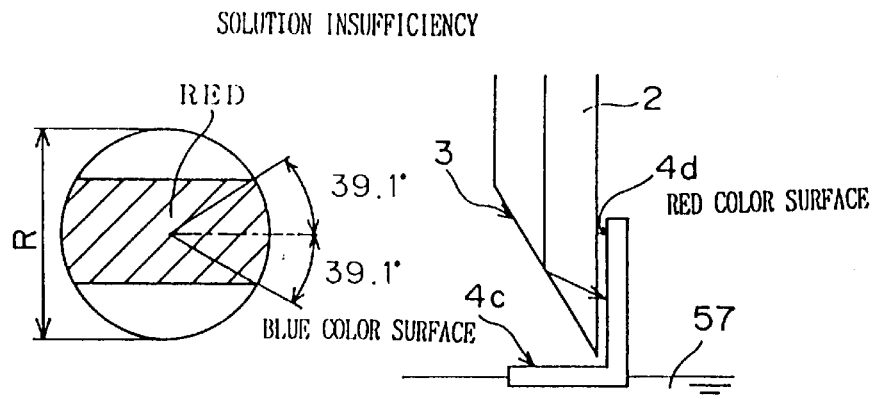
FIG. 4, consisting of FIGS. 4A to 4C, is a view for explaining a light path and a display pattern related to the first embodiment of the present invention.
Figure 4B:
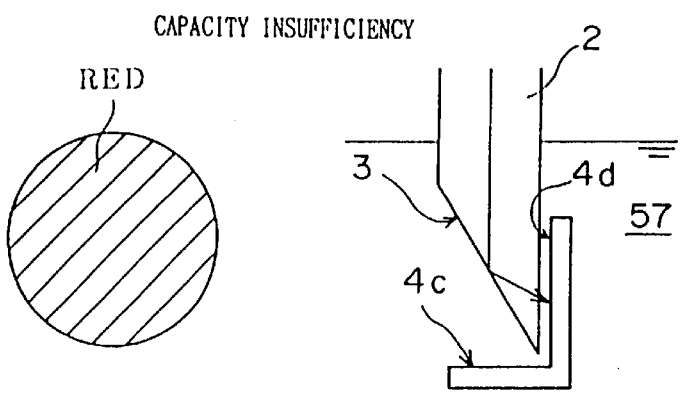

As shown in FIG. 4A, in the case where the electrolytic solution 57 is insufficient, that is, the surface level of the electrolytic solution 57 lowers and the whole pillar member 2 is exposed outside, the incident light transmitting from the one end 11 side is reflected totally toward the side of the pillar member 2. The reflected light, in the case where the operator looks from the upper side 11 of the display member 2, advances almost vertically toward the outer circumferential surface of the pillar member 2. However, since the pillar member 2 is shaped to provide a column and, in the case where the light advances from the pillar member 2 to air, the critical angle is $\phi=39.1°$ according to sin $\phi=1/1.585$, the incident light having an incident angle which is larger than $\phi=39.1°$ is reflected toward the inner side of the pillar member 2 by the outer circumference section of the pillar member 2 and the incident light having an incident angle except for the incident angle which is larger than $\phi=39.1°$ permeates through 63% of the center area of the section width R of pillar member 2 according to Rsin $\phi=0.6309R$. Since the only permeating light through the center portion is projected onto the red surface 4d of the display member 4, when the operator looks into the end surface of one side 11 of the display member 2 from the upper side thereof, the center area of the end surface is shown in red. Moreover, as shown in FIG. 4B, in the case where the capacity of the storage battery 50 is insufficient, that is, the specific gravity of the electrolytic solution 57 is no more than 1.19, the incident light transmitting from the one end 11 side is reflected totally toward the side of the pillar member 2. Because the electrolytic solution 57 is in contact with the outer circumference surface of the pillar member 2, the incident light having an incident angle which is larger than the critical angle about 60° is reflected toward the inner side of the pillar member 2 by the outer circumference section of the pillar member 2. Therefore, the incident light permeates through the whole area of the section width of pillar member 2. Since the permeating light through the whole area is projected onto the red surface 4d of the display member 4, when the operator looks into the end surface of one side 11 of the display member 2 from the upper side thereof, the whole area of the end surface is shown in red.

Figure 4C:
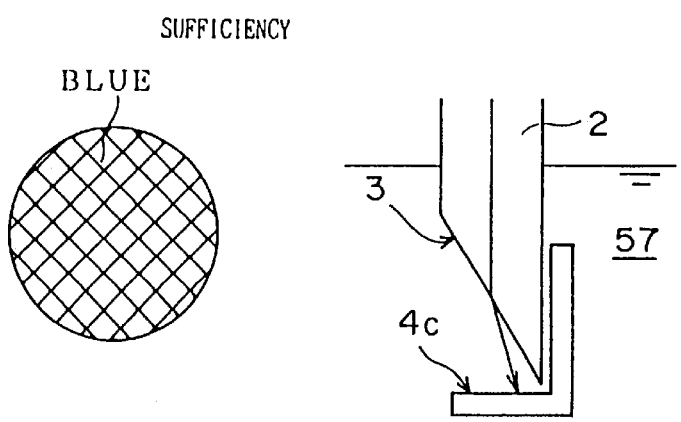

Furthermore, as shown in FIG. 4C, in the case where the charging supply of the storage battery 50 is sufficient, that is, the specific gravity of the electrolytic solution 57 is not less than the specific gravity of 1.19 by which the inclined angle is set, the incident light transmitting from the one end 11 side permeates through the inclined surface 3 by the refracting angle in accordance with the specific gravity of the electrolytic solution 57 so that the incident light is projected onto the blue surface 4c of the display member 4. As a result, when the operator looks into the end surface of one side 11 of the display member 2 from the upper side thereof, the whole area of the end surface is shown in blue.

As mentioned above, in the display device of the storage battery related to this embodiment, because the inclined surface is formed at the opposite end of the pillar surface and the display member is provided at the opposite end thereof, it is possible to detect the charging condition through a simple structure without using a movable portion, making it possible to reduce the detecting errors, to manufacture the display device easily, and to reduce the manufacturing cost of the display device.

(Second embodiment)

A second preferred embodiment of the present invention will be described hereunder with reference to the illustrations of FIGS. 5 to 7.

This second embodiment, similar to the first embodiment, shows a display device of the present invention which is applied to a lead storage battery.

Figure 5A:
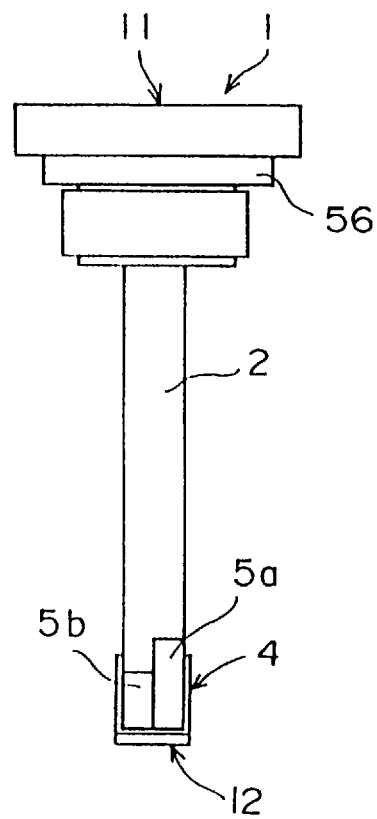
FIG. 5A is a side view of the storage battery related to a second embodiment of the present invention and FIG. 5B is a longitudinal sectional view related to the second embodiment of the present invention.
Figure 5B:
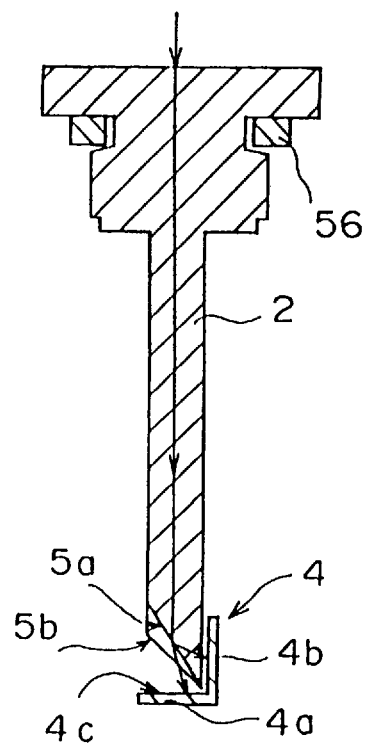
Figure 6:
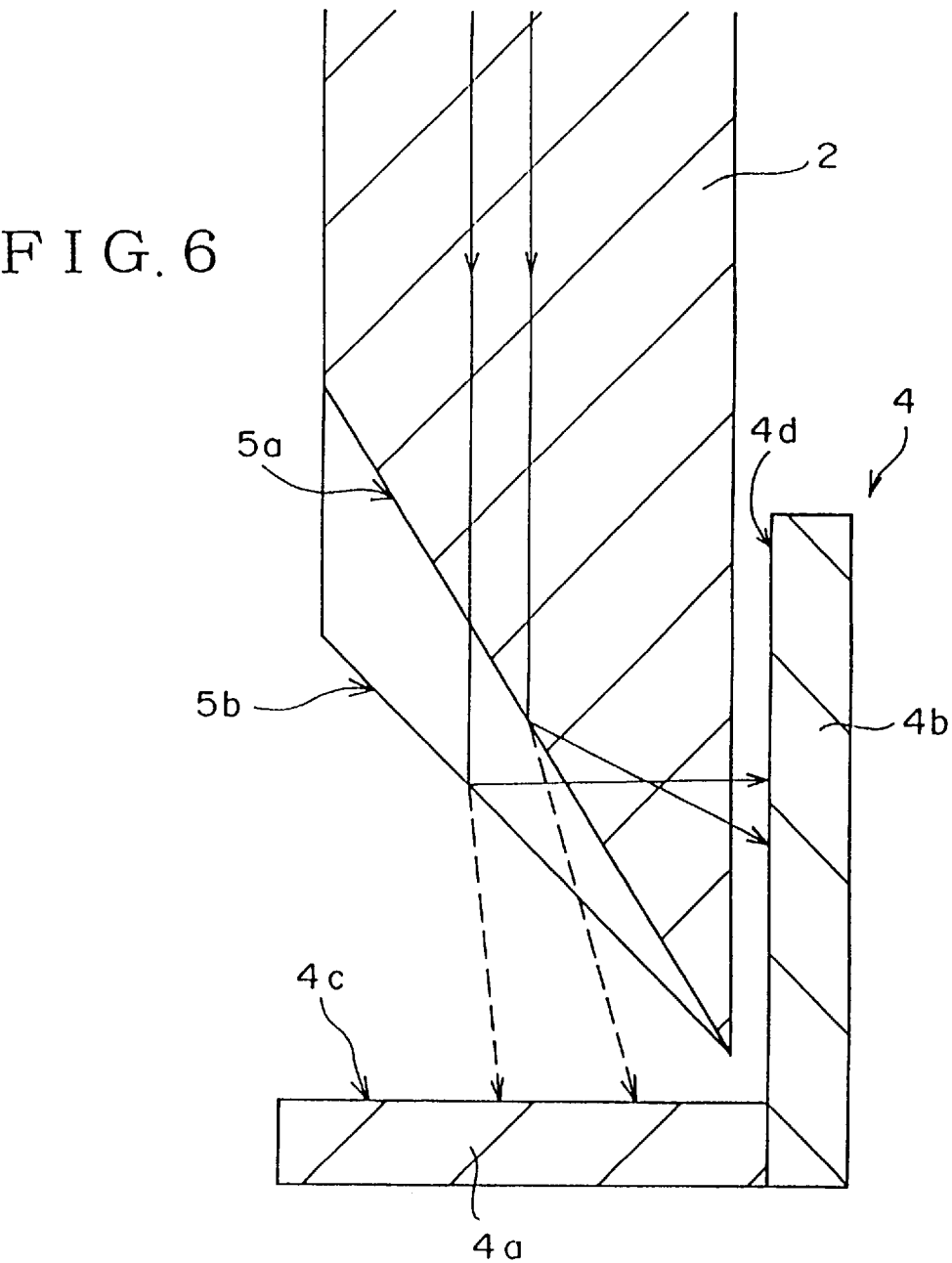
FIG. 6 is a longitudinal sectional view, in an enlarged scale, of a portion of the display device shown in FIG. 5B.

Referring to FIGS. 5 to 7, a display device 1 related to the present embodiment is constructed such that the pillar member 2 shaped like a column, having a rectangular cross-section. The rectangular pillar member 2 is provided at its opposite end 12 with two inclined surfaces 5a and 5b which are different from each other. The inclination angle of the inclined surface 5a is set, as similar to the first embodiment, so that, when the specific gravity of the electrolytic solution 57 is 1.19, the incident angle of the light transmitting from the one end 11 side on the inclined surface 5a is a critical angle. Moreover, in the case where the electrolytic solution 57 of an insufficient charging supply condition is in contact with the inclined surface 5b, the inclination angle of the inclined surface 5b is set so that, when the specific gravity of the electrolytic solution 57 is 1.0, the incident angle of the light transmitting from the one end 11 side on the inclined surface 5b is the critical angle.

For example, the concrete inclination angle of the inclined surface 5b will be set as follows. In the case where the rectangular pillar member 2 is made of polycarbonate, the refractive index of polycarbonate n1 is 1.585. Because the specific gravity of the electrolytic solution 57 for which the charging supply is sufficient is no more than 1.18, the specific gravity of 1.0 which is much smaller than the specific gravity of the 1.18 is used. That is, in the case where the specific gravity of the electrolytic solution 57 is 1.0, since the refractive index n2 thereof is 1.333, the critical angle is φ=57.25° according to n2/n1=sin φ. Therefore, because the inclination angle of the inclined surface 5b is set so that the incident angle of the incident light transmitting from the one end 11 side on the inclined surface is the critical angle of nearly 57° and in the case where the electrolytic solution 57 is not in contact with the inclined surface 3 because of the insufficiency of the electrolytic solution 57, the inclined surface 3 reflects the light totally. In addition, in the case where the charging supply of the electrolytic solution 57 is sufficient, the light permeates through the inclined surface 5b. Since the other structures of the display device of this embodiment are substantially the same as that of the first embodiment, the explanation of the other structures thereof is omitted.

Next, the display condition of the structure of the display device 1 in this second embodiment will be described hereunder.

Figure 7A:
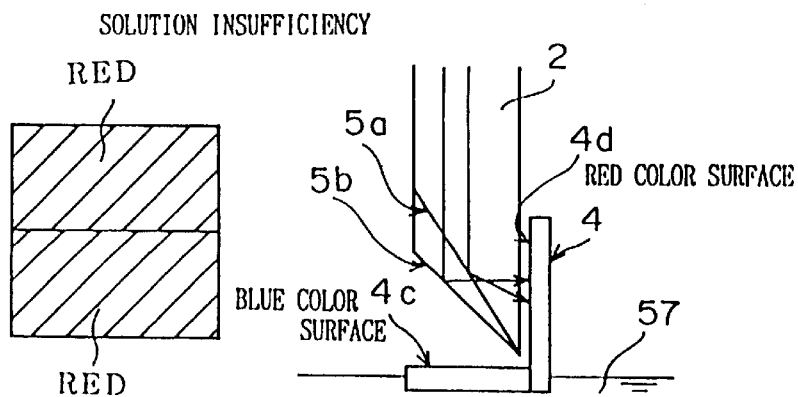
FIG. 7, consisting of FIGS. 7A to 7C, is a view for explaining a light path and a display pattern related to the second embodiment of the present invention.

As shown in FIG. 7A, in the case where the electrolytic solution 57 is insufficient, that is, the surface level of the electrolytic solution 57 lowers and the whole pillar member 2 is exposed outside, the incident light transmitting from the one end 11 side is reflected totally by both of the inclined surfaces 5a and 5b toward the side of the pillar member 2. The reflected light permeates through the outer circumferential surface of the rectangular pillar member 2 toward the outside thereof so that the incident light is projected onto the red surface 4d of the display member 4. As a result, when the operator looks into the end surface of one side 11 of the display member 2 from the upper side thereof, the whole area of the end surface is shown in only red.

Figure 7B:
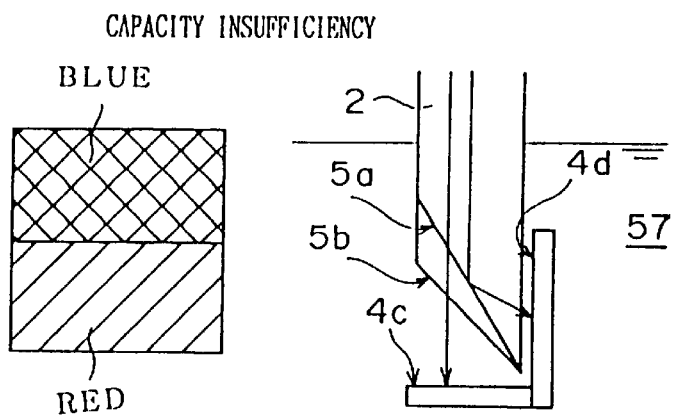

Moreover, as shown in FIG. 7B, in the case where the capacity of the storage battery 50 is insufficient, that is, the specific gravity of the electrolytic solution 57 is no more than 1.19, the incident light transmitting from the one end 11 side is reflected totally by the inclined surface 5a toward the side of the pillar member 2. However, in the other inclined surface 5b, because the specific gravity of the electrolytic solution 57 is not less than the specific gravity of 1.0 by which the inclined angle thereof is set, the incident light transmitting from the one end 11 side permeates through the inclined surface 5b with the refracting angle in accordance with the specific gravity of the electrolytic solution 57. The reflected light from the inclined surface 5a permeates through the outer circumferential surface of the rectangular pillar member 2 toward the outside thereof so that the reflected light is projected onto the red surface 4d of the display member 4. On the other hand, the reflected light from the inclined surface 5b is projected onto the blue surface 4c of the display member 4. Therefore, when the operator looks into the end surface of one side 11 of the display member 2 from the upper side thereof, the whole area of the end surface is shown in red and blue.

Figure 7C:
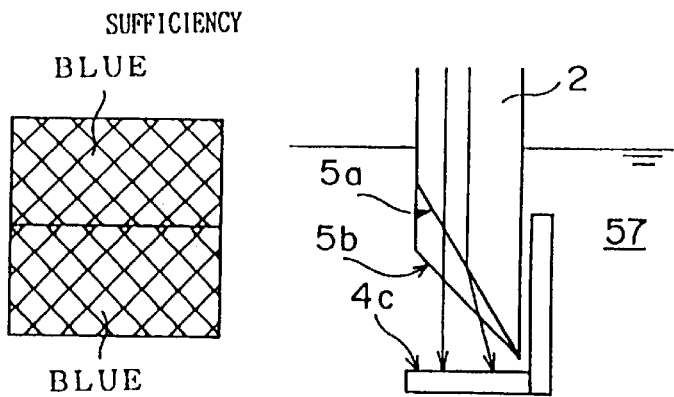

Furthermore, as shown in FIG. 7C, in the case where the charging supply of the storage battery 50 is sufficient, that is, the specific gravity of the electrolytic solution 57 is not less than the specific gravity 1.19, since the specific gravity thereof is larger than the specific gravity by which each of the inclined angles of the inclined surfaces 5a and 5b is set, the incident light transmitting from the one end 11 side permeates through the inclined surfaces 5a and 5b with the refracting angle in accordance with the specific gravity of the electrolytic solution 57 so that the incident light is projected on the blue surface 4c of the display member 4. As a result, when the operator looks into the end surface of one side 11 of the display member 2 from the upper side thereof, the whole area of the end surface is shown in only blue. As mentioned above, in this second embodiment, as similar to the first embodiment, it is enables to detect the charging condition with a simple structure without using a movable portion, making it possible to reduce the detecting errors, to manufacture the display device easily, and to reduce the manufacturing cost of the display device.

Furthermore, in the display device of the storage battery related to this embodiment, because the inclination angles of the inclined surfaces 5a and 5b are different from each other, it is possible to make different the condition of the reflection from that of the penetration according to each of the phases of the level of the specific gravity and the surface level of the electrolytic solution 57. Therefore, since the display phase gained by the display device of this embodiment is closed, it is possible to distinguish the charging conditions of the electrolytic solution 57 clearly.

(Third embodiment)

A third preferred embodiment of the present invention will be described hereunder with reference to the illustrations of FIGS. 8 to 10.

This third embodiment, similar to the first embodiment, shows a display device of the present invention which is applied to a lead storage battery.

Figure 8A:
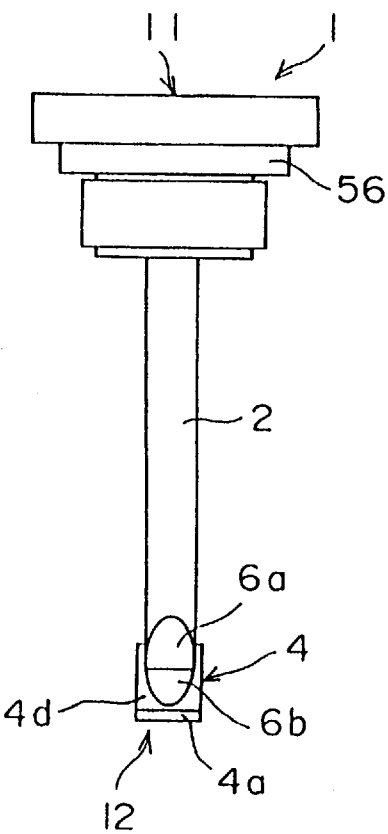
FIG. 8A is a side view of the storage battery related to a third embodiment of the present invention and FIG. 8B is a longitudinal sectional view related to the third embodiment of the present invention.
Figure 8B:
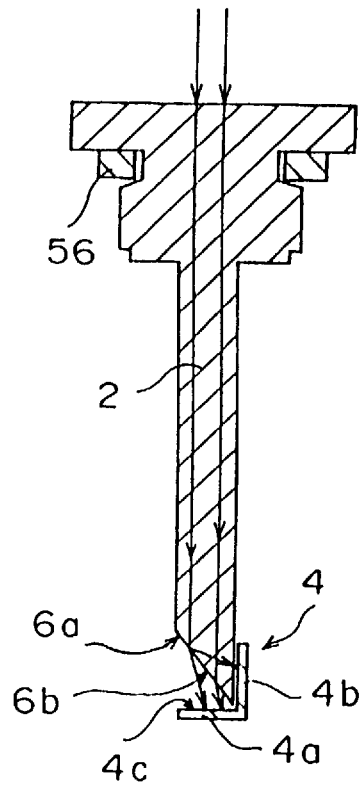
Figure 9:
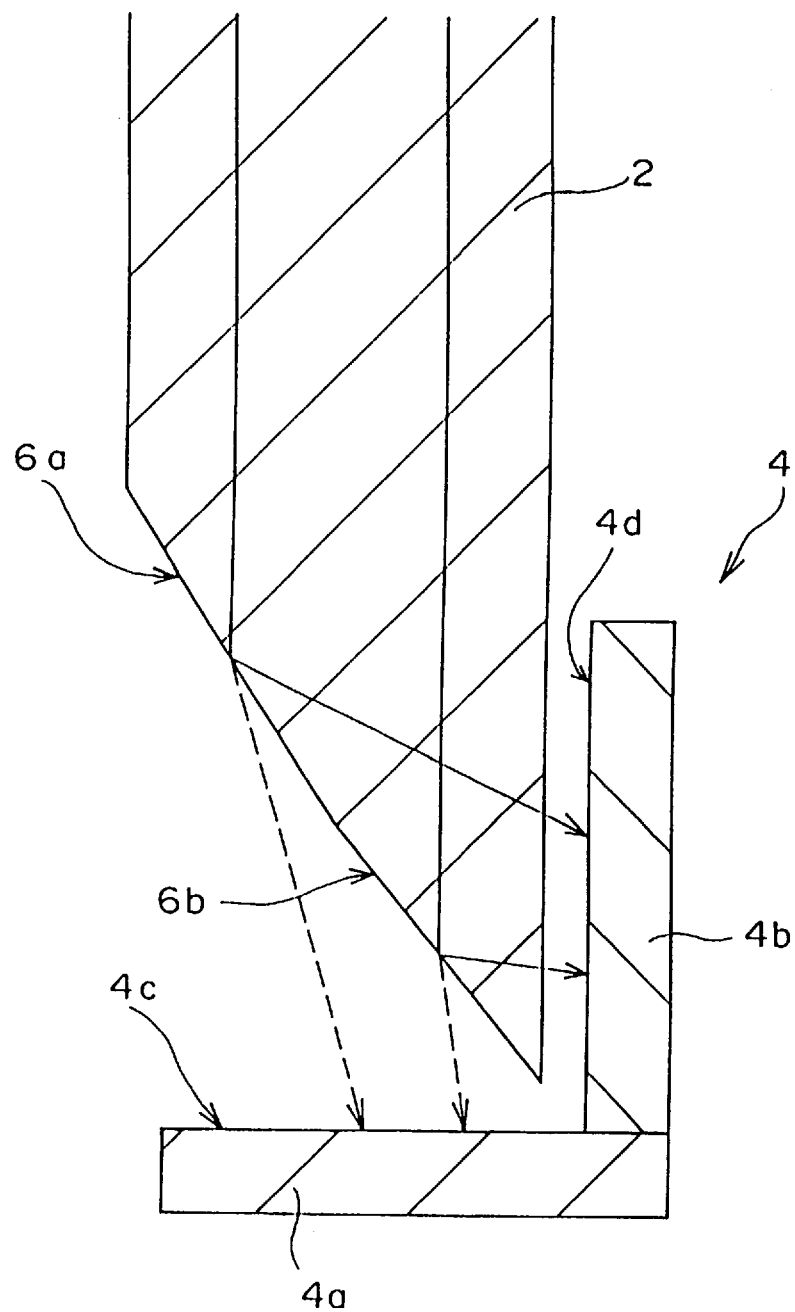
FIG. 9 is a longitudinal sectional view, in an enlarged scale, of a portion of the display device shown in FIG. 8B.

Referring to FIGS. 8 to 10, a display device 1 related to the present embodiment is constructed in such a manner that the inclined surface 3 provided at the opposite end 12 of the pillar member 2 is replaced with a double inclined surface which has double stages, which are continuously inclined to the side surface of the pillar member 2 at different predetermined angles, respectively. The first stage of the inclined surface is consisted of the first inclined surface 6a and the second step thereof is consisted of the second inclined surface 6b connected to the first inclined surface 6a. The second inclined surface 6b is positioned below with the first inclined surface 6a, and the inclined angle of the inclined surface 6b is smaller than that of the inclined surface 6a. The inclined angle of the lower second inclined surface 6b is set, as similar to the first embodiment, so that, when the specific gravity of the electrolytic solution 57 is 1.19, the incident angle of the light transmitting from the one end 11 side on the inclined surface 6b is the critical angle. Moreover, the inclined angle of the upper first inclined surface 6a is set so that, when the specific gravity of the electrolytic solution 57 is 1.26, the incident angle of the light transmitting from the one end 11 side on the inclined surface 6a is the critical angle.

For example, the concrete angle of the first inclined surface 6a is set as follows. In the case where the pillar member 2 is made of polycarbonate, the refractive index of polycarbonate n1 is 1.585. Because the specific gravity of the electrolytic solution 57 of the sufficient charging supply condition is within the limit of 1.19 to 1.26, the higher limit value of 1.26 of the specific gravity thereof is used. That is, in the case where the specific gravity of the electrolytic solution 57 is 1.26, since the refractive index n2 thereof is 1.379, the critical angle is φ=60.46° according to n2/n1=sin φ. Therefore, since the inclination angle of the first inclined surface 6a is set so that the incident angle of the incident light transmitting from the one end 11 side on the inclined surface is the critical angle of about 60°, in the case where the electrolytic solution 57 is not in contact with the first inclined surface 6a because of the insufficiency of the electrolytic solution 57 and the specific gravity of the electrolytic solution 57 which is in contact with the inclined surface 3 is smaller than the upper limit value thereof, the inclined surface 6a reflects the light totally. In addition, in the case where the charging supply of the electrolytic solution 57 has been completed, the specific gravity of the electrolytic solution 57 being larger than the upper limit value thereof, the light permeates through the inclined surface 6a.

Since the other structures of the display device of this third embodiment are substantially the same as those of the first embodiment, the explanation of the other structures thereof is omitted.

Next, the display condition of the structure of the display device 1 in this third embodiment will be described hereunder.

Figure 10A:
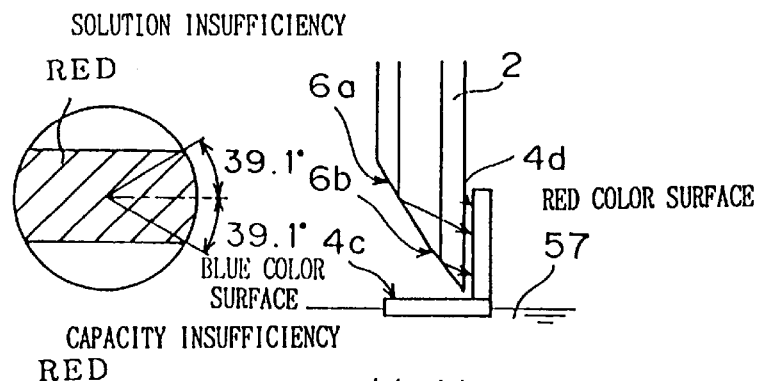
FIG. 10, consisting of FIGS. 10A to 10D, is a view for explaining a light path and a display pattern related to the third embodiment of the present invention.

As shown in FIG. 10A, in the case where the electrolytic solution 57 is insufficient, that is, the surface level of the electrolytic solution 57 lowers and the whole pillar member 2 is exposed outside, the incident light transmitting from the one end 11 side is reflected totally by both of the inclined surfaces 6a and 6b toward the side of the pillar member 2. The reflected light by the inclined surfaces 6a and 6b moves toward the side of the pillar member 2. Since there is air in the outer side of the pillar member 2, the critical angle is small and since the pillar member 2, as similar to the first embodiment, is shaped like the column, the incident light having an incident angle which is larger than $\phi=39.1°$ is reflected toward the inner side of the pillar member 2 by the outer circumference section of the pillar member 2, and the incident light having an incident angle except for the incident angle which is larger than $\phi=39.1°$ permeates through the center area of the section width of pillar member 2. Since only the permeating light through the center portion is projected onto the red surface 4d of the display member 4, when the operator looks into the end surface of one side 11 of the display member 4 from the upper side thereof, only the center area of the end surface is shown in red.

Figure 10B:
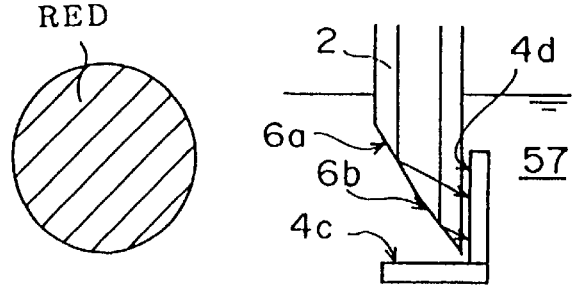

Furthermore, as shown in FIG. 10B, in the case where the capacity of the storage battery 50 is insufficient, that is, the specific gravity of the electrolytic solution 57 is no more than 1.19, the incident light transmitting from the one end 11 side is reflected totally by both the inclined surfaces 6a and 6b. Since the electrolytic solution 57 is in contact with the outer circumferential surface of the pillar member 2, the light reflected by the inclined surfaces 6a and 6b permeates through the whole area of the outer circumferential section of the pillar member 2 toward the outside thereof so that the reflected light is projected onto the red surface 4d of the display member 4. Therefore, when the operator looks into the end surface of one side 11 of the display member 2 from the upper side thereof, the whole area of the end surface is shown in red.

Figure 10C:
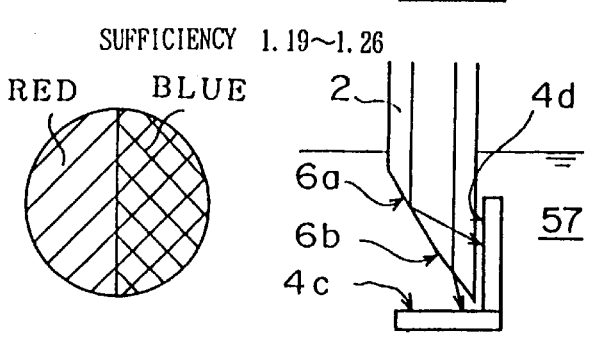

Furthermore, as shown in FIG. 10C, in the case where the charging supply of the storage battery 50 is sufficient, that is, the specific gravity of the electrolytic solution 57 is not less than the specific gravity of 1.19 and is no more than the specific gravity of 1.26, since the specific gravity of the electrolytic solution 57 is not less than the specific gravity of 1.19, the incident light transmitting from the one end 11 side is reflected totally by the first inclined surface 6a toward the side of pillar member 2. However, in the second inclined surface 6b, since the specific gravity of the electrolytic solution 57 is larger than the specific gravity of 1.19 by which the inclined angle of the inclined surface 6b is set, the incident light transmitting from the one end 11 side permeates through the second inclined surface 6b by the refracting angle in accordance with the specific gravity of the electrolytic solution 57. The reflected light from the first inclined surface 6a permeates through the outer circumferential surface of the rectangular pillar member 2 toward the outside thereof so that the reflected light is projected onto the red surface 4d of the display member 4. On the other hand, the light reflected by the inclined surface 6b is projected onto the blue surface 4c of the display member 4. Consequently, when the operator views the end surface of one side 11 of the display member 2 from the upper side thereof, the whole area of the end surface is shown in red and blue.

Figure 10D:
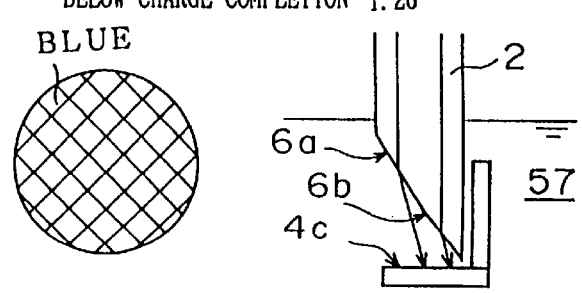

In addition, as shown in FIG. 10D, in the case where the charging supply of the storage battery 50 has been completed, that is, the specific gravity of the electrolytic solution 57 is not less than the specific gravity 1.26, because the specific gravity thereof is larger than the specific gravity by which each of the inclined angles of the inclined surfaces 6a and 6b is set, the incident light transmitting from the one end 11 side permeates through the inclined surfaces 6a and 6b with the refracting angle in accordance with the specific gravity of the electrolytic solution 57 so that the incident light is projected onto the blue surface 4c of the display member 4. As a result, when the operator views the end surface of one side 11 of the display member 2 from the upper side thereof, the whole area of the end surface is shown in only blue.

Moreover, in this third embodiment, the inclined surface has double stages, but the present invention is not limited to such structure, and the inclined surface may have plural stages.

As mentioned above, the display device of the storage battery related to this embodiment has the same effects as those attained by the first embodiment. Moreover, in the display device related to this embodiment, since the inclined surface is formed as the surface which has the plural stages, it is possible to divide the advancing direction of the light transmitting from the one end side so as to part the display phases according to the conditions of the electrolytic solution 57. Therefore, it is possible to display the conditions of the electrolytic solution 57 in detail.

More particularly, in the first, second, and third embodiments, the display device is of a type mounted in the upper cover of the storage battery. However, present invention is not limited to such type of the display device, and the display device may have an electrical surf ace level sensor installed therein and the display device may also be used for the liquid stoppers such as liquid plug which has a vent structure. In this case, since the pillar member body forms mainly the portion through which a light can permeate, the cap part and the screw part of the display device which are provided at the portion except for the pillar member may be formed of other opaque material in the case where, when the operator views the end surface of the pillar member from the upper side thereof, the cap part and the screw part thereof do not interrupt the view of the operator.

(Forth embodiment)

A fourth preferred embodiment of the present invention will be described hereunder with reference to the illustration of FIGS. 11 to 14. This fourth embodiment shows a display device of the present invention which is applied to a lead storage battery.

Referring to FIGS. 11 to 14, a display device related to the present embodiment has a transparent pillar member 70 formed of transparent polycarbonate, AS resin, acrylic resin, or other similar material, the display member 70 being shaped like a column.

The one end 81 side (the upper end side) is expanded like a flange. A rubber packing 72 is fitted into the one end 81 side, which is fitted with the upper cover 102 having electrodes 103 and 104 and liquid stoppers such as liquid plug 105. An electrolytic solution 107 is stored in a casing 101 of the storage battery 100.

The electrolytic solution 107 is not leaked out of the casing 101 with the rubber packing 106 even if the electrolytic solution 107 is vibrated. The opposite end 82 side (lower end side) of the pillar member 70 is usually immersed in the electrolytic solution 107.

Figure 11A:
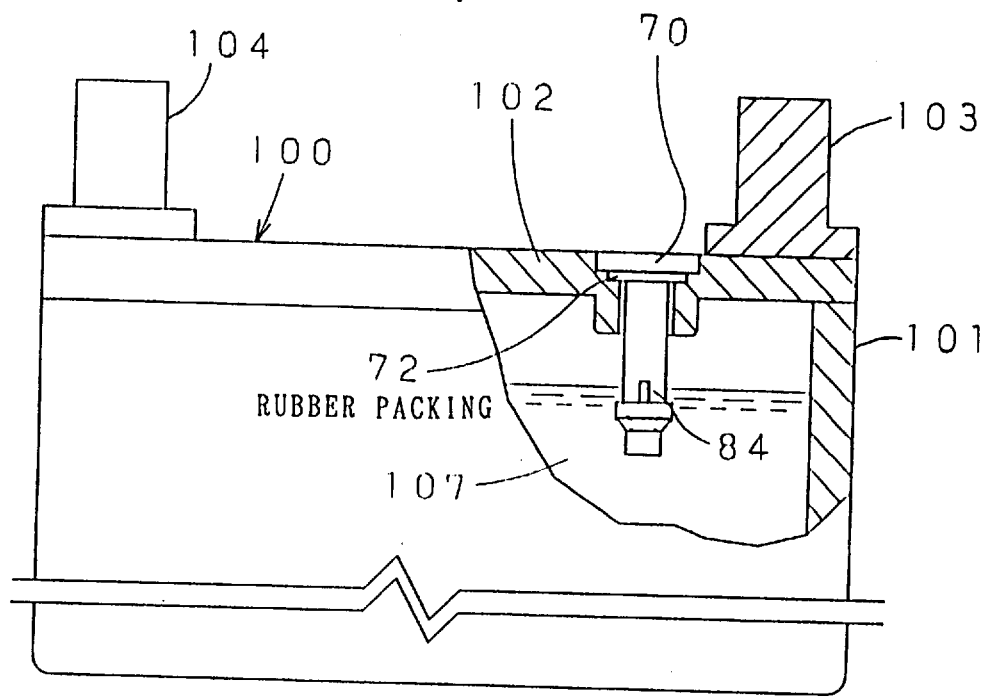
FIG. 11A is a front view of a storage battery fitted with a display device partially broken away, the display device being related to a fourth embodiment of the present invention
Figure 11B:
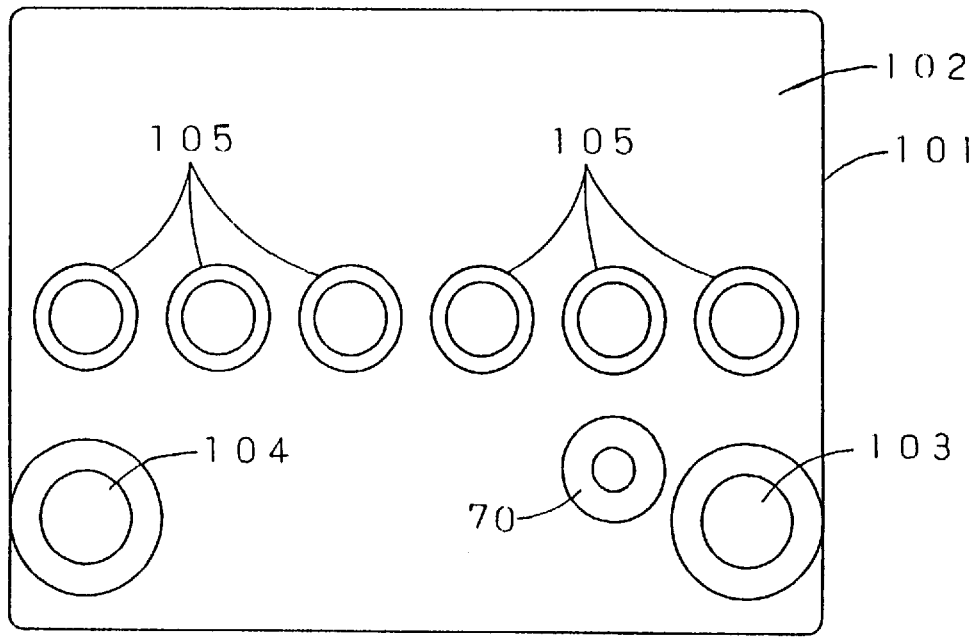
FIG. 11B is a plan view of the storage battery fitted with the display device related to the fourth embodiment of the present invention.

A communication hole portion 77 is communicated with the electrolytic solution 107 in the casing 101 and is formed at the center portion of the opposite end 82 side of the pillar member 70. The electrolytic solution 107 in the casing 101 is introduced into the communication hole portion 77 which is shaped like a column. An inclined surface 73 is formed on the outer peripheral surface of the pillar member 70 defining the outer periphery of the communication hole portion 77. The lower end of the opposite end 82 side of the pillar member 70 is opened and a lower portion holder 76 like a cap is mounted on the lower end thereof. The lower holder portion 76 is formed in shape of cap made of synthetic resin material and having an inner surface colored with white. The lower holder portion 76 is secured to the lower end of the communication hole portion 77 of the pillar member 70 through fitting or welding process. The upper portion of the lower holder portion 76 is coated under the condition of tightly contacting to the upper portion of the inclined surface 73 of the pillar member 70 to thereby prevent the inclined surface 73 from being contaminated by the electrolytic solution 107. Further, it is to be noted that the upper portion of the lower holder portion 76 is formed to provide a hollow structure such that the upper portion is not entirely contacted to the inclined surface 73, contacted only to the upper and lower edge portions thereof, and separated therefrom at the intermediate portion between the upper and lower edge portions. In this structure, it is also prevent the inclined surface 73 from being contaminated. Solution introducing holes 80 are formed to the bottom surface of the lower portion holder 76 for introducing the electrolytic solution 107 into the communicating hole portion 77. A pair of solution introducing holes 84 are provided, as shown in FIG. 11, at the right side of the communication hole portion 77 and the left side thereof, respectively.

In the communication hole portion 77, specific gravity balls 74 and 75 having predetermined specific gravities, respectively are provided, the specific gravity balls 74 and 75 being arranged along a center axis of the pillar member 70 in a line so as to rise and lower in accordance with the change of the surface level and the specific gravity of the electrolytic solution 107 in the communication hole portion 77.

The specific gravity of the upper side specific gravity ball 74 along the axis is set to 1.19 and is colored with an opaque fluorescent pigment, the color of which is red. The specific gravity of the lower side specific gravity ball 75 along the axis is set to 1.22 and is colored with an opaque fluorescent pigment, the color of which is green.

At the upper end portion of the communication hole portion 77, a projection portion 78 is formed so that the projection portion 78 projects into the inside of the communication hole portion 77. The projecting portion 78 is shaped like a rod and the pointed end of the projecting portion 78 is shaped like a cone. The pointed end surface of the projecting portion 78 is adapted to form a center inclined surface 79. The inclination angle of the center inclined surface 79, when the electrolytic solution 107 is in contact with the center inclined surface 79, is set so that the incident light transmitting from the one end side 81 along the center axis of the pillar member 70 permeates through the center inclined surface 79 toward the lower side of the center inclined surface 79. On the other hand, when the electrolytic solution 107 is not in contact with the center inclined surface 79, the inclination angle of the center inclined surface 79 is set so as to reflect the incident light totally thereby twice, the incident light being returned toward the one end side 81.

Figure 12:
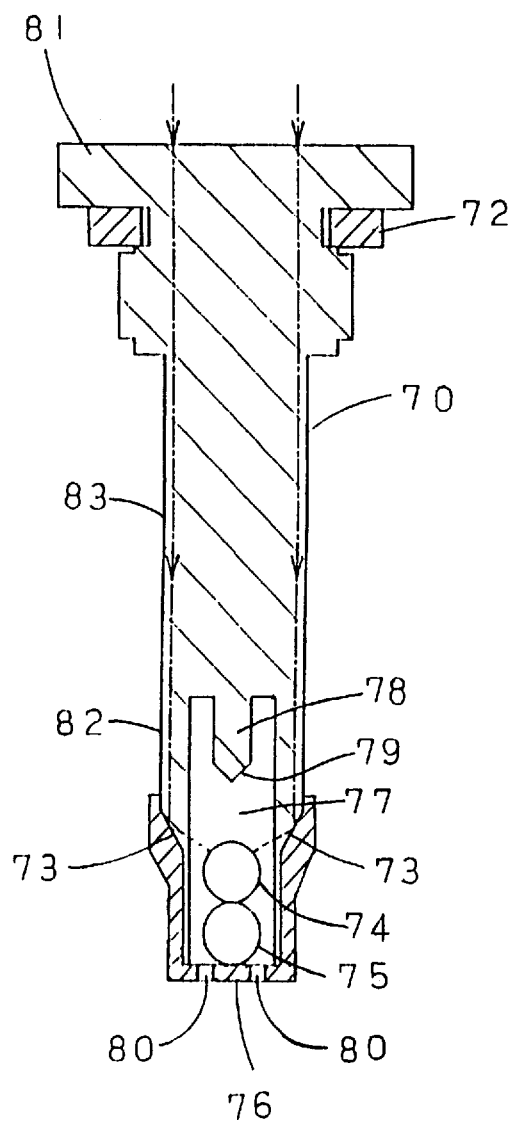
FIG. 12 is a longitudinal sectional view related to the fourth embodiment of the present invention.
Figure 13:
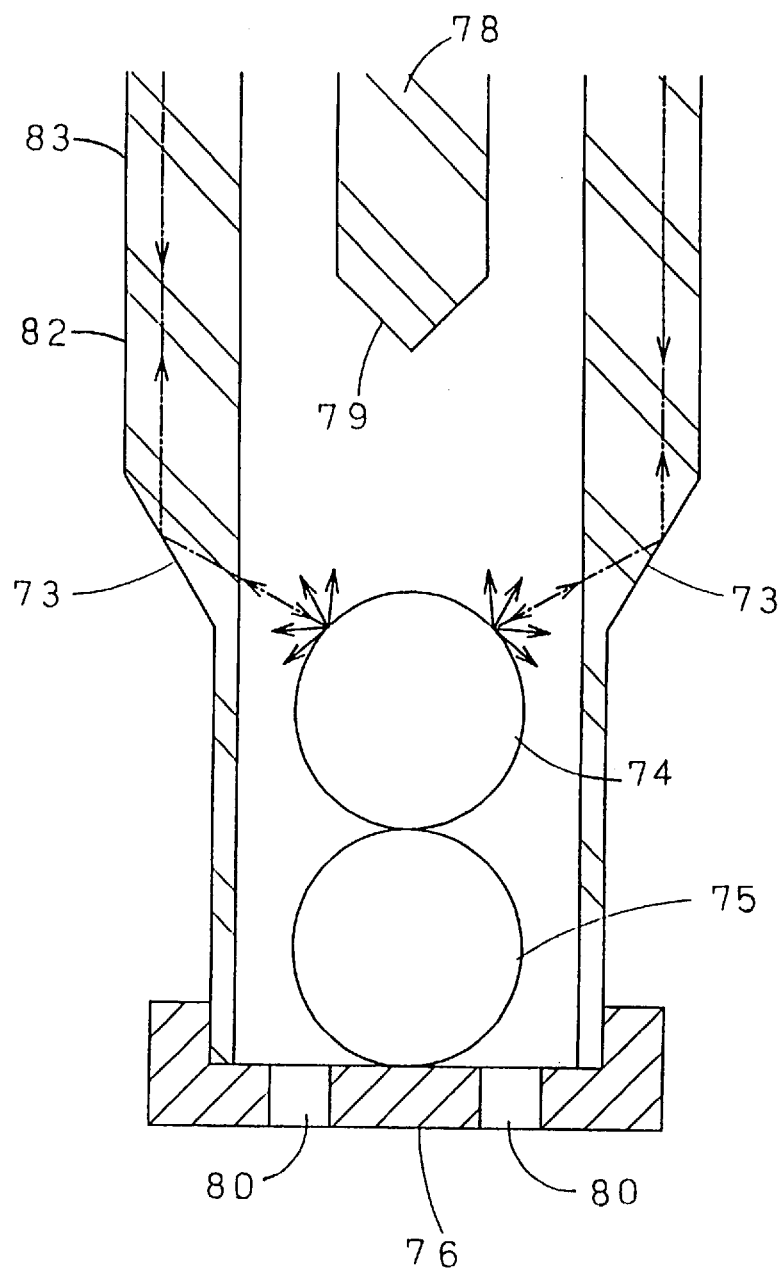
FIG. 13 is a longitudinal sectional view, in an enlarged scale, of a portion of the display device shown in FIG. 12.

As shown in FIGS. 12 and 13 in an enlarged scale, the outer circumference surface of the pillar member 70 which is adjacent to the communication hole portion 77 is inclined inward in taper against the side surface 83 thereof so that the outer circumference surface thereof is formed as an inclined surface 73. When the electrolytic solution 107, which has the largest refractive index in the case of the complete sufficiency of the electrolytic solution 107 is in contact with the inclined surface 73, the inclination angle of the inclined surface 73 is set so as to reflect the light transmitting from the one end 81 side totally by the inclined surface 73. For example, the concrete inclination angle of the inclined surface is set as follows. In the case where the pillar member 70 is made of polycarbonate, the refractive index of polycarbonate $n1$ is 1.585.

Because the refractive index $n2$ of the electrolytic solution 107, in the case where the specific gravity of 1.3 thereof is larger than the specific gravity of 1.28 thereof for which the charging supply is completely sufficient, is 1.368, the critical angle is $I=60.98°$ according to $n2/n1=\sin I$. Therefore, when the inclined angle is set so that the incident angle of the light transmitting from the one end 81 side on the inclined surface is much larger critical angle of about 61°, the inclined surface 3 reflects the incident light totally toward the side of the communication hole portion 77 at all times. Moreover, when the specific gravity balls 74 and 75 fall down, the reflected light collide vertically with the spherical surface of the specific gravity ball 74. On the other hand, when the specific gravity balls 74 and 75 rise up, the reflected light collide vertically with the spherical surface of the specific gravity ball 75.

Furthermore, the case where the incident angle of the inclined surface 73 is about 60° is only one example, and it is possible to set the incident angle I at any optional angle in accordance with the quality of the material of the pillar member 70 and the characteristic feature of the electrolytic solution 107.

Figure 14A:
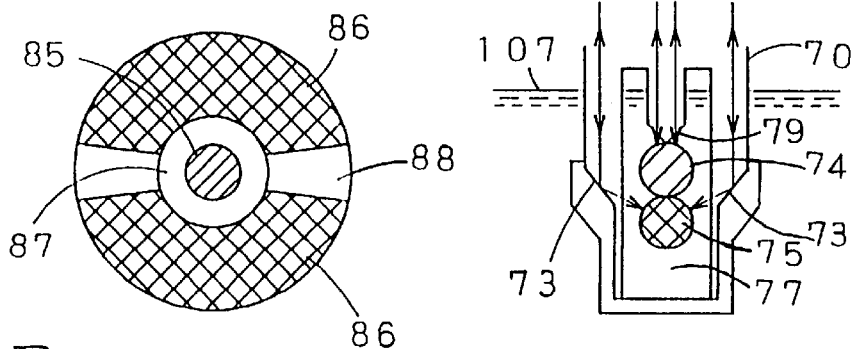
FIG. 14, consisting of FIGS. 14A to 14D, is a view for explaining a light path and display pattern according to various conditions of an electrolytic solution related to the fourth embodiment of the present invention.

Next, the display condition of the structure of the display device in this fourth embodiment will now be described with reference to FIGS. 14A to 14D. As shown in FIG. 14A, when the charging supply of the lead storage battery 100 is fully sufficient, since the specific gravity of the electrolytic solution 107 is larger than the specific gravity of 1.22 of the lower green specific gravity ball 75, not only the upper specific gravity ball 74 but also the lower specific gravity ball 75 rise up so that the specific gravity ball 74 is located at the reflection layer of the communication hole portion 77. This layer is irradiated by the light reflected totally by the inclined surface 73. Therefore, the incident light transmitting from the one end 81 side and reflected totally by the inclined surface 73 is projected onto the specific gravity ball 75. A part of the light projected onto the specific gravity ball 75, as shown in FIG. 13, is reflected by the surface thereof randomly, but the most part of the light projected thereon moves backward so as to be returned toward the one end side 81. Accordingly, green fluorescence appears in the outer circumference surface of the end surface 81. Moreover, the incident light, which is incident along the center axial direction of the pillar member 70 from the center portion 85 of the end surface of the one end 81 side thereof, permeates through the center inclined surface 79 and is reflected by the red specific gravity ball 75 so that the incident light permeates through the center inclined surface again and the permeating light is returned toward the center portion 85 of the end surface 81 of the one end 81 side. As a result, dark red appears in the center portion 85 of the end surface of the one end 81 side. The circular portion 87 of the end surface of the one end 81 side corresponds to the communication hole portion 87 of the outside circumference of the projection portion 78 and the wing portion 88 extending in shape of wing to right and left sides from the circular portion 87 corresponds to the solution introducing hole 84 of the pillar member 70.

Figure 14B:
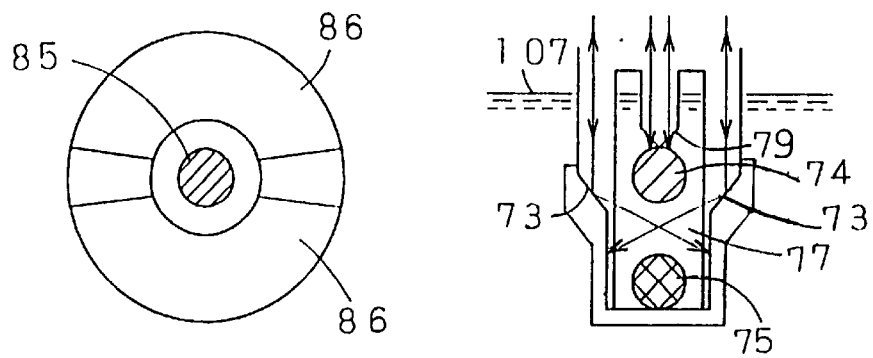

As shown in FIG. 14B, when the charging supply of the lead storage battery 100 is sufficient and the specific gravity of the electrolytic solution 107 is no less than that of 1.19 and is no more than the specific gravity of 1.22, since the specific gravity of the electrolytic solution 107 is no more than 1.22, the green specific gravity ball 75 having the specific gravity of 1.22 falls down so that the light reflected by the inclined surface 73 advances straight without colliding against the specific gravity ball 75 and is irradiated to the inner surface of the lower holder portion 76. Therefore, white appears in the outer circumferential portion 86 of the end surface 81 by the white color reflected by the white inner surface of the lower holder portion 76. In the center portion 85 of the end surface of the one end 81 side, as the same in FIG. 14A, dark red appears.

Figure 14C:
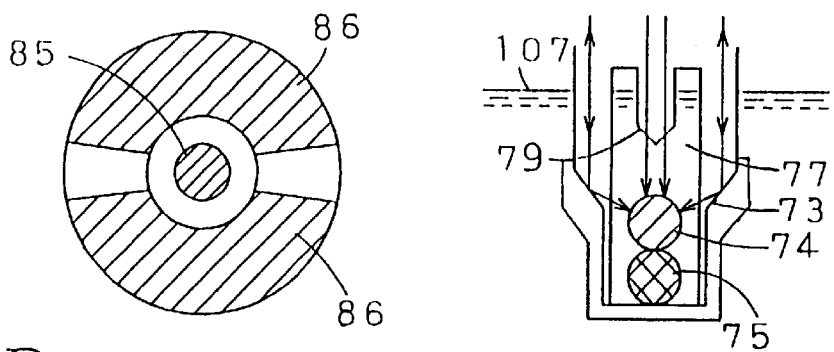

As shown in FIG. 14C, when the charging supply of the lead storage battery 100 is insufficient due to an electric discharge and the specific gravity of the electrolytic solution 107 is no more than the specific gravity of 1.19, since the red specific gravity ball 74 having the specific gravity of 1.19 falls down, the light reflected totally by the inclined surface 73 collide against the specific gravity ball 74. Thus, red appears in the outer circumference portion 86 of the end surface 81. On the other hand, because the incident light which is incident on the center inclined surface 79 is not nearly reflected totally thereby, the center portion 85 of the end surface of the one end 81 side is dark.

Figure 14D:
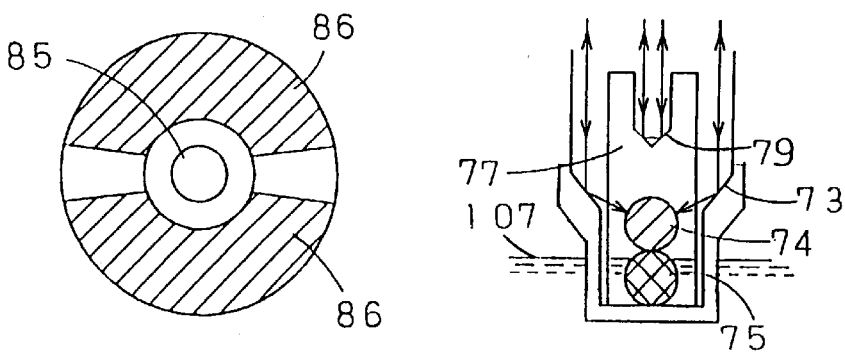

As shown in FIG. 14D, since the electrolytic solution 107 is insufficient and the surface level of the electrolytic solution 107 in the communication hole portion 77 is low, the specific gravity balls 74 and 75 fall down, respectively. Therefore, in the outer circumference portion 86 of the end surface of the one end 81 side appears in red due to the return light which is reflected by the red specific gravity ball 74. On the other hand, the incident light which is incident on the center inclined surface 79 is reflected totally thereby twice so that the advancing direction of the incident light turns by about 180° and the incident light is returned toward the center portion 85 of the one end side 81. Therefore, in the center portion 85 of the end surface of the one end 81 side, white appears.

(Fifth embodiment)

A fifth preferred embodiment of the present invention, will be described hereunder with reference to FIG. 15.

This fifth embodiment is constructed so that the specific gravity of the electrolytic solution is displayed by means of a light permeating through a specific gravity ball.

In this embodiment, the specific gravity of the upper side specific gravity ball 74 is set by 1.0, the surface of the specific gravity ball 74 being colored in red, and the specific gravity of the lower side specific gravity ball 75 is set by 1.19, the surface of the specific gravity ball 75 being colored in blue. Since the other structures of the display device of this embodiment are substantially the same as those of the fourth embodiment, the explanation of the other structures thereof is omitted.

Figure 15A:
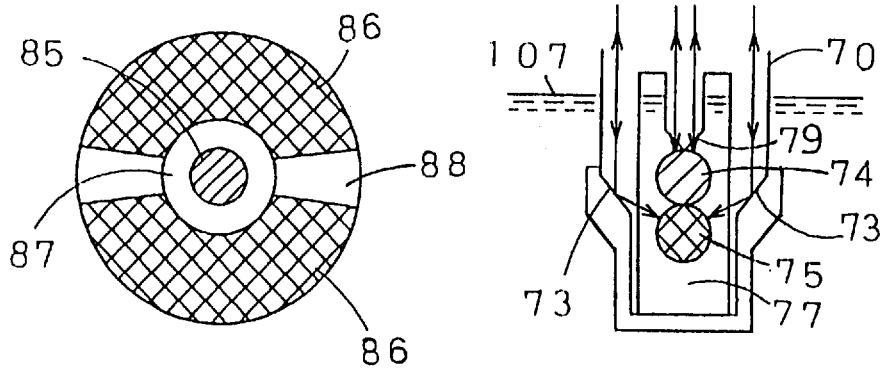
FIG. 15, consisting of FIGS. 15A to 15C, is a view for explaining a light path and display pattern according to various conditions of an electrolytic solution related to a fifth embodiment of the present invention.

As shown in FIG. 15A, when the charging supply of the lead storage battery 100 is sufficient and the specific gravity of the electrolytic solution 107 is no less than the specific gravity of 1.19, and the specific gravity of the electrolytic solution 107 is no less than the specific gravity of 1.19, the blue specific gravity ball 75 rises up so that the light reflected totally by the inclined surface 73 is projected onto the specific gravity ball 75. The reflected light is returned again toward the one end side 81 so that blue fluorescence appears in the outer circumference portion of the end surface 81. On the other hand, the incident light which is incident on the center inclined surface 79 permeates through the center inclined surface 79 and is reflected by the specific gravity ball 74 so that the incident light permeates through the center inclined surface again, the permeating light is returned toward the center portion 85 of the end surface of the one end 81 side. As a result, dark red appears in the center portion 85 of the end surface of the one end 81 side.

Figure 15B:
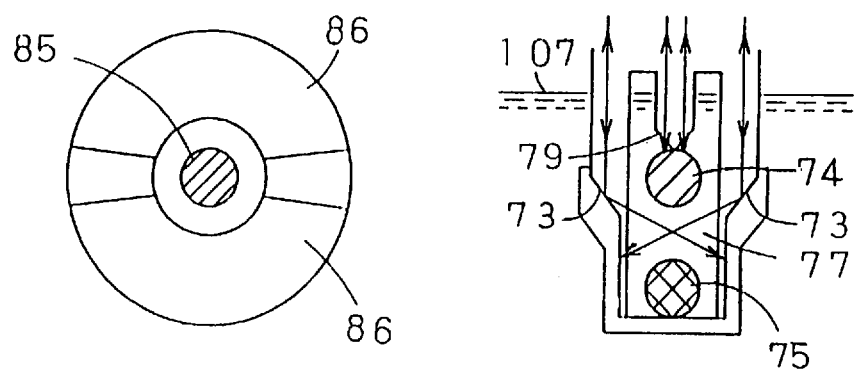

As shown in FIG. 15B, when the charging supply of the lead storage battery 100 is insufficient due to an electric discharge and the specific gravity of the electrolytic solution 107 is no more than the specific gravity of 1.19, the specific gravity ball 75 having the specific gravity of 1.19 sinks, but the specific gravity ball 74 having the specific gravity of 1.0 is maintained in its floating state in the electrolytic solution 107. For this reason, both the specific gravity balls 74 and 75 are not located at the reflection layer of the communication hole portion 77, the light which is reflected totally by the inclined surface 73 advances straight and is irradiated on the inner surface of the lower holder portion 76. Therefore, the outer circumferential portion 86 of the end surface of the end surface of the end portion 81 appears white by the white light reflected by the white inner surface of the lower holder portion 76. On the other hand, in the center portion 85, dark red appears due to the light reflected by the specific gravity ball 74.

Figure 15C:
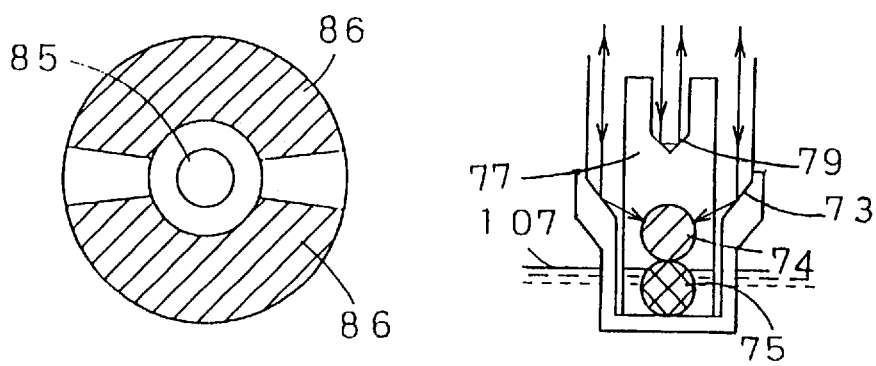

As shown in FIG. 15C, since the electrolytic solution 107 is insufficient and the surface level of the electrolytic solution 107 in the communication hole portion 77 is low, the specific gravity balls 74 and 75 sink, respectively. In this case, the light reflected totally by the inclined surface 73 is hit on the red specific gravity ball 74 and the reflected light is returned toward the one end side 81 so that red appears in the outer circumference portion 86 of the end surface thereof. In addition, the incident light which is incident on the center inclined surface 79 is reflected totally thereby twice so that the advancing direction of the incident light turns by 180° and the incident light is returned toward the center portion 85. Therefore, in the center portion 85 of the end surface of the one end 81 side, white appears.

(Sixth embodiment)

Figure 16:
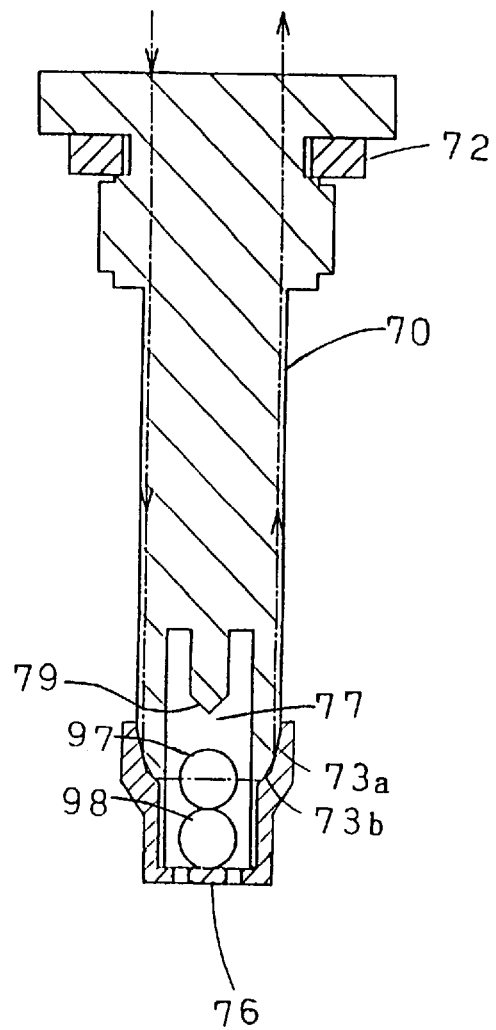
FIG. 16 is a longitudinal sectional view related to a sixth embodiment of the present invention.
Figure 17:
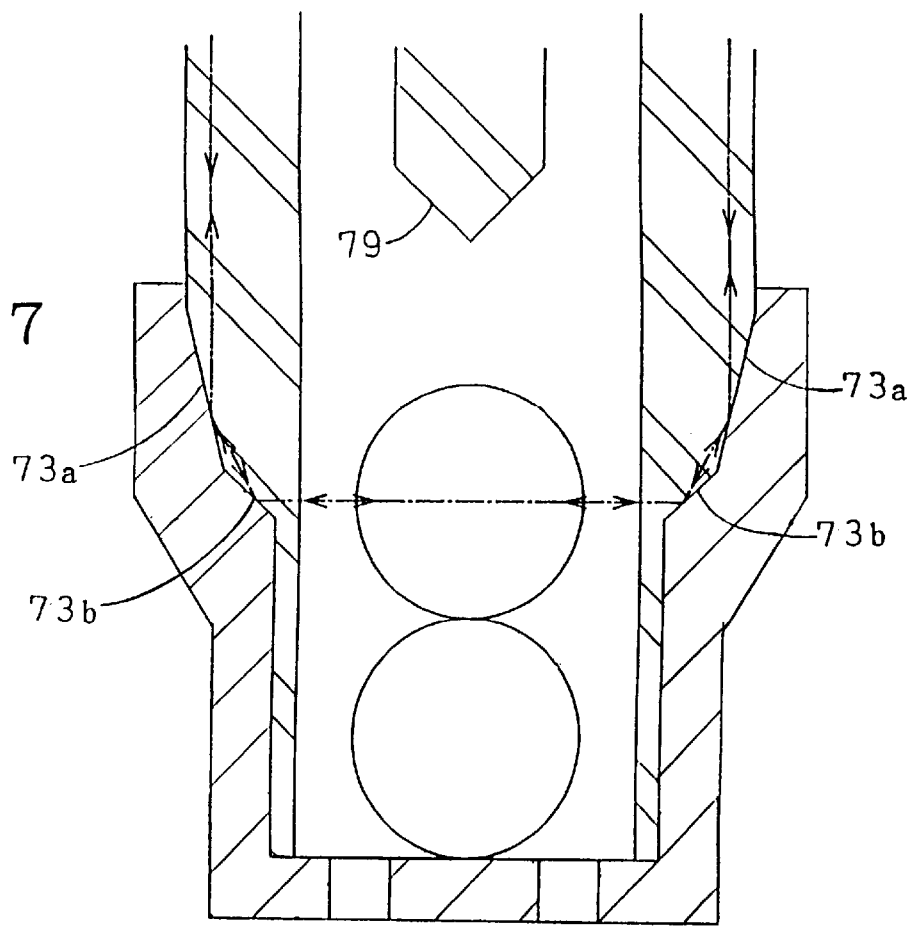
FIG. 17 is a longitudinal sectional view, in an enlarged scale, of a portion of the display device shown in FIG. 16.
Figure 18:
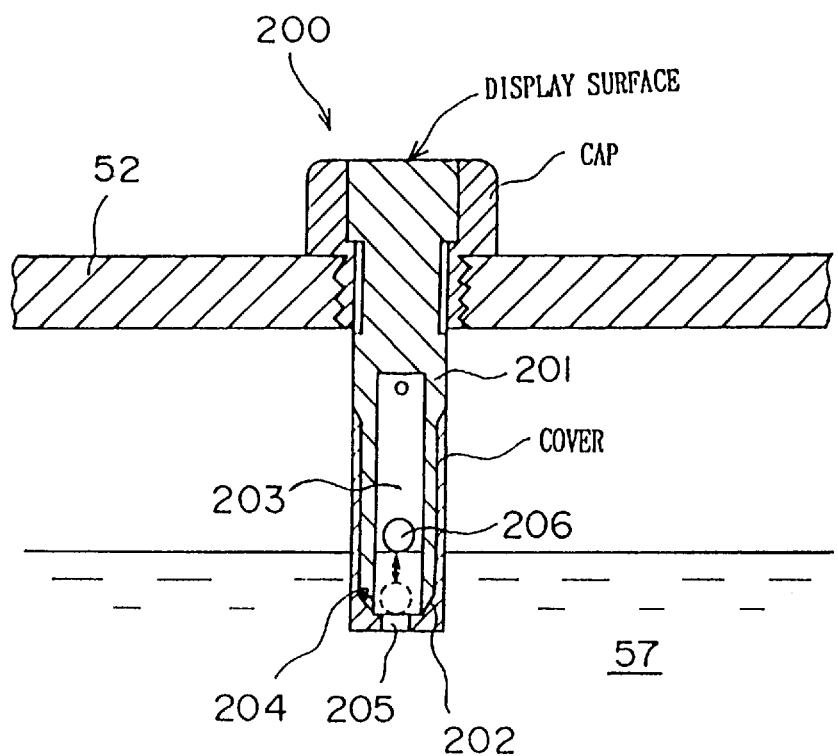
FIG. 18 is a schematically structural view showing a conventional display device for a storage battery.

A sixth preferred embodiment of the present invention, will be described hereunder with reference to the illustration of FIGS. 16 to 17. This sixth embodiment is constructed so that the specific gravity of the electrolytic solution is displayed by means of a light permeating through a specific gravity ball. Therefore, the structure of the specific gravity ball and the inclined surface is different from that of the fourth embodiment or fifth embodiment, but the other structures of the display device of the sixth embodiment are substantially the same as those of the fourth embodiment or fifth embodiment.

A specific gravity balls 97 and 98 formed of colored transparent material which is red, blue, or other similar color, having a predetermined specific gravity, respectively. An inclined surface for hitting the light reflected totally by the inclined surface, as shown in FIGS. 16 and 17 in an enlarged scale of FIG. 16, consists of a double inclined surface which has double stages, which continuously incline to the side surface of the pillar member 70 at different predetermined angles, respectively. The first stage of the inclined surface is consisted of the first inclined surface 73a and the second stage thereof is consisted of the second inclined surface 73b connected to the first inclined surface 73a. The second inclined surface 73b is positioned below the first inclined surface 73a and the inclination angle of the inclined surface 73b is smaller than that of the inclined surface 73a. In this structure, the incident light which is incident on the inclined surface is reflected totally by the first inclined surface 73a and the second inclined surface 73b twice so as to turn the advancing direction of the incident light on the large angle to the direction crossing to the direction of the center axis of the pillar member 70 and to hit the incident light horizontally from the side of the specific gravity balls 97 and 98 on the side surface thereof which is opposite to inner side surface of the pillar member 70.

Each of the lights permeating through the specific gravity balls 97 and 98 is reflected totally by the second inclined surface again. Therefore, the light is returned to the outer circumference portion of the end surface of the end 81 side so that a predetermined color appears in the outer circumference portion of the end 81 side. The display phase due to the returned light from the center inclined surface 79 is the same as those of the fourth and fifth embodiments.

Moreover, in this sixth embodiment, the inclined surface has double stages, but the present invention is not limited by such structure. That is, the inclined surface may have other plural stages.

As mentioned above, in the display device of the storage battery related to the forth, fifth, and sixth embodiments, since the inclined surface which is the outer side surface of the pillar member is formed as the total reflection surface so as to display the specific gravity of the electrolytic solution for displaying the charging condition of the storage battery, it is possible to display the charging condition by mere the simple structure, making it possible to manufacture the display device easily and to improve the quality of the display device and the yield thereof. Furthermore, since the large quantity of light can be projected onto the specific gravity balls and the large quantity of light reflected thereby or permeating therethrough is reflected totally by the inclined surface of the outside of the communication hole portion so as to return the total reflected light toward the end side of the pillar member, large and bright image can be gained, thereby improving the performance of the display device. In addition, because the specific gravity balls which rise up and lower in the communication hole portion according to the surface level of the electrolytic solution and specific gravity thereof are formed to each provide a spherical shape, the rising and lowering movements of the specific gravity balls are done smoothly, thereby preventing the detecting errors and the incorrect displaying operation of the display device from causing.

Furthermore, since the specific gravity and color of the specific gravity balls are different from each other, it is possible to display the various conditions of the specific gravity and surface level of the electrolytic solution clearly in plural colors so as to distinguish each conditions by different colors.

Moreover, since it is possible to detect the rising and falling condition of the specific gravity balls or the surface level of the electrolytic solution from the center inclined surface side, it is possible to display the various conditions of the electrolytic solution in detail. Especially, in the sixth embodiment, because the inclined surface is formed as the surface having a plurality of stages, the total reflection of the incident light on the inclined surface is performed in plural times so that the advancing direction of the incident light can be turned on the large angle. Therefore, this structure is suitable for displaying the specific gravity of the electrolytic solution by the permeating light which is incident toward the transparent specific gravity balls from the side thereof and hit thereon so as to permeate therethrough.

More particularly, in the sixth embodiment, since the specific gravity balls formed of the transparent material which is formed to provide a spherical shape, it is performed to display the condition of the specific gravity of the storage battery by means of the light which permeates through the specific gravity balls, instead of the light which is reflected thereby, and is returned toward the end side of the pillar member, making it possible to display the various conditions of the specific gravity of the electrolytic solution clearly.

In addition, in the fourth, fifth, and sixth embodiments, since the outer circumference portion 86 of the pillar member 70 and the center portion 85 thereof are mainly formed as light permeating portion, it may be possible to replace the other portions of the pillar member 70 except for the outer circumference portion 86 and the center portion 85 thereof with a hollow portion which has a hollow structure. Therefore, for example, a hollow portion is formed at the circular portion 87 or a center part including the center portion 85 with the center inclined surface 79 being omitted so as to install the electrically surface level sensor in the center part. Moreover, the display device may also be used for the liquid stoppers which has a vent structure.

Furthermore, according to the fourth, fifth and sixth embodiments, the solution introducing hole 80 is formed to the bottom surface of the lower holder the lower holder portion 76, but it may be possible to form the solution introducing hole 80 as a tapered opening hole opened outwardly upward to the side surface of the lower holder portion 76 and the bottom surface thereof is not provided with any opening. In such arrangement, any air bubble dose not invade from the bottom surface of the lower holder portion 76, and the air bubble will easily escape outside through the upwardly opened solution introducing hole 80 formed to the side surface of the lower holder portion 76, whereby the air bubble does not invade into the communication hole portion 77 side and, hence, the elevational motion of the specific gravity balls at the communication hole portion will not be affected by the air bubble, thus eliminating an occurrence of display error and improving the reliability of measurement.

Still furthermore, in the respective embodiments, the lower holder portion 76 mounted on the other end side 82 of the pillar member may be formed of a transparent material in place of the formation of the synthetic resin material having an inner surface which is colored with white. In the case of the transparent lower holder portion 76, the color of the inside wall of the casing 51 is displayed as a display color in the case of FIG. 14B in which light is not projected on the specific gravity balls 74 and 75. Further, an optional color other than white and different from the color of the specific gravity balls 74 and 75 may be selected for the color of the inner surface of the lower holder portion 76.

It will be further understood by those skilled in the art that the foregoing description is made by way of preferred embodiments of the display device illustrated in the accompanying drawings and that various changes and modifications may be made according to the present invention without departing from the spirit and scope of the appended claims.

What is claimed is:

1. A display device for a storage battery for optically displaying a condition of an electrolytic solution stored in a casing of the storage battery, the device comprising:

a pillar member having a transparent body having one end and another opposite end, said one end of the pillar member being engaged at an upper surface of the casing in a usable state so that the other opposite end is projected into the casing, said transparent body of the pillar member having an inclined end surface located on the opposite end side having an inclination to a side surface of the pillar member at a predetermined angle so that an incident light transmitting from one end side thereof permeates through the inclined end surface or is reflected according to a condition of the electrolytic solution which is in contact with the inclined end surface; and a display member provided with a plurality of display surfaces on which the light permeating through the inclined end surface or reflected thereby is projected, said display surfaces being different from each other to optically display the condition of the electrolytic solution wherein said display member is provided at proximate the one end side of the pillar member.

2. A display device for a storage battery according to claim 1, wherein each of said display surfaces is colored.

3. A display device for a storage battery according to claim 1, wherein the condition of the electrolytic solution includes at least a specific gravity of the electrolytic solution and a surface level thereof.

4. A display device for a storage battery according to claim 1, wherein the predetermined angle of the inclined end surface is set so that an incident angle of the incident light transmitting from the one end side on the inclined end surface is a predetermined critical angle.

5. A display device for a storage battery according to claim 4, wherein said critical angle is set in accordance with a quality of a material of the pillar member and a characteristic feature of the electrolytic solution.

6. A display device for a storage battery according to claim 1, wherein said inclined end surface is provided with a plurality of inclined surface portions, which are inclined to the side surface of the pillar member at different predetermined angles, respectively.

7. A display device for a storage battery according to claim 1, wherein said inclined end surface has a plurality of stages, which are continuously inclined to the side surface of the pillar member at different predetermined angles, respectively.

8. A display device for a storage battery for optically displaying a condition of an electrolytic solution stored in a casing of the storage battery, the device comprising:

a pillar member having a transparent body having one end and another opposite end, said one end of the pillar member being engaged at an upper surface of the casing in a usable state so that the other opposite end thereof is projected into the casing, said other opposite end being formed with a communication hole portion communicated with the electrolytic solution in the casing, through which the electrolytic solution is introduced into the pillar member; and a specific gravity ball unit disposed in the communication hole portion, said specific gravity ball unit having a predetermined specific gravity and rising and falling along a center axis of the communication hole portion in accordance with at least one of a surface level of the electrolytic solution in the communication hole portion and the specific gravity thereof, wherein said specific gravity ball unit includes a plurality of spherical balls having specific gravities different from each other and being colored in different colors so that the displayed condition of the electrolytic solution is changed in accordance with the rising and lowering movement of each of the spherical balls, said transparent body of the pillar member having an inclined surface located on an opposite end side of the pillar member having an inclination to a side surface of the pillar member at a predetermined angle so as to reflect an incident light transmitting from the one end side thereof totally toward a communication hole portion side so as to optically display the condition of the electrolytic solution.

9. A display device for a storage battery according to claim 8, wherein the displayed condition of the electrolytic solution is changed according to the rising and lowering movement of the specific gravity ball unit.

10. A display device for a storage battery according to claim 8, wherein said communication hole portion is formed substantially at a center portion of the opposite end side of the pillar member.

11. A display device for a storage battery according to claim 8, wherein said specific gravity ball unit is formed of a transparent material.

12. A display device for a storage battery according to claim 8, wherein said predetermined angle of the inclined surface is set so that an incident angle of the incident light transmitting from the one end side on the inclined end surface is a predetermined critical angle.

13. A display device for a storage battery according to claim 12, wherein said critical angle is set in accordance with a quality of a material of the pillar member and a characteristic feature of the electrolytic solution.

14. A display device for a storage battery according to claim 8, wherein said inclined surface has a plurality of stages which are continuously inclined to the side surface of the pillar member at different predetermined angles, respectively.

15. A display device for a storage battery according to claim 8, further comprising a projecting portion formed so as to project into an upper end portion of the communication hole portion, said projecting portion having a pointed end portion formed to provide a cone shape so as to incline a surface of the pointed end portion at a predetermined angle so that the incident light transmitting from the one end side thereof permeates through the inclined surface of the pointed end portion or is reflected thereby according to the condition of the electrolytic solution which is in contact with the inclined surface thereof.

* * * * *